(12) United States Patent
O'Cearbhaill et al.

(10) Patent No.: US 12,121,442 B2
(45) Date of Patent: Oct. 22, 2024

(54) IMPLANTABLE MEDICAL DEVICE

(71) Applicant: University College Dublin, National University of Ireland, Dublin, Dublin (IE)

(72) Inventors: Eoin O'Cearbhaill, Dublin (IE); Fergal Coulter, Dublin (IE)

(73) Assignee: University College Dublin, National University of Ireland, Dublin (IE)

( * ) Notice: Subject to any disclaimer, the term of this patent is extended or adjusted under 35 U.S.C. 154(b) by 693 days.

(21) Appl. No.: 16/617,707

(22) PCT Filed: May 4, 2018

(86) PCT No.: PCT/EP2018/061513
§ 371 (c)(1),
(2) Date: Nov. 27, 2019

(87) PCT Pub. No.: WO2018/219590
PCT Pub. Date: Dec. 6, 2018

(65) Prior Publication Data
US 2020/0179121 A1 Jun. 11, 2020

(30) Foreign Application Priority Data
May 29, 2017 (EP) .................................. 17173244

(51) Int. Cl.
*A61F 2/30* (2006.01)
*A61L 27/18* (2006.01)
(Continued)

(52) U.S. Cl.
CPC .......... *A61F 2/30756* (2013.01); *A61L 27/18* (2013.01); *A61L 27/20* (2013.01);
(Continued)

(58) Field of Classification Search
CPC ........ A61F 2/30756; A61F 2002/30766; A61F 2/022; A61L 27/18; A61L 27/20;
(Continued)

(56) References Cited

U.S. PATENT DOCUMENTS 5,545,223 A 8/1996 Neuenfeldt et al.
5,585,613 A 12/1996 Bell et al.
(Continued)

OTHER PUBLICATIONS

Barnsley et al., "Textured Surface Breast Implants in the Prevention of Capsular Contracture among Breast Augmentation Patients: A Meta-Analysis of Randomized Controlled Trials" Plastic and Reconstructive Surgery 2006, 117(7): 2182-2190.
(Continued)

*Primary Examiner* — Yashita Sharma
(74) *Attorney, Agent, or Firm* — Kelly A. Barton; Casimir Jones, S.C.

(57) ABSTRACT

The invention broadly provides an implantable medical device comprising a liquid rope coil scaffold. The implant may consist essentially of the scaffold, where the scaffold is the implant and pores in the scaffold may incorporates one or more agents (i.e. drugs, growth factors), or the scaffold may comprise only part of the medical device, for example an implant that is partly or fully covered with a layer of the scaffold. The porosity of the scaffold may be tailored to suit the application, for example a porosity that is tailored to hold and release drug or biological molecules in vivo, a porosity to provide a surface roughness that is conducive to promotion of in-vivo bio-integration (for example vascularisation) or prevention of fibrosis, or a porosity that provides structural strength. The scaffold may be essentially tubular, or may be provided as a planar structure, or may be any shape and can be used to coat, fully or partially any shape or size of medical implant.

10 Claims, 11 Drawing Sheets

(a) Monocoque implementation (b) Removable inner pouch implementation

(51) Int. Cl.
*A61L 27/20* (2006.01)
*A61L 27/38* (2006.01)
*A61L 27/54* (2006.01)
*A61L 27/56* (2006.01)

(52) U.S. Cl.
CPC ........... *A61L 27/3834* (2013.01); *A61L 27/54* (2013.01); *A61L 27/56* (2013.01); *A61F 2002/30766* (2013.01); *A61L 2300/62* (2013.01); *A61L 2300/64* (2013.01)

(58) Field of Classification Search
CPC ...... A61L 27/3834; A61L 27/54; A61L 27/56; A61L 2300/62; A61L 2300/64; A61L 27/3804; C12N 2535/00; C12N 5/0012; C12N 5/0068; C12N 2533/30; A61K 35/12; A61K 2035/126
See application file for complete search history.

(56) References Cited

U.S. PATENT DOCUMENTS

| | | | |
|---|---|---|---|
| 8,129,182 B2 | 3/2012 | D'Amour et al. | |
| 9,079,337 B2 | 7/2015 | Lipton et al. | |
| 9,132,226 B2 | 9/2015 | Martinson et al. | |
| 9,724,447 B2 | 8/2017 | Karp et al. | |
| 2003/0175410 A1* | 9/2003 | Campbell | A61L 27/38 623/23.72 |
| 2005/0152950 A1* | 7/2005 | Saffran | A61M 1/3673 623/1.42 |
| 2009/0078003 A1 | 3/2009 | Cook | |

OTHER PUBLICATIONS

Brun, "Liquid Ropes: A Geometrical Model for Thin Viscous Jet Instabilities" Phys. Rev. Lett. 114, 174501 (2015).

Crivello & Reichmanis, "Photopolymer Materials and Processes for Advanced Technologies" Chemistry of Materials, 26(1):533-548.

Dunlop et al. "A theoretical model for tissue growth in confined geometries." J. Mech Phys Solids 2010, 58: 1073-1087.

Food and Drug Administration, Questions and Answers about Breast Implant-Associated Anaplastic Large Cell Lymphoma (BIA-ALCL), retrieved from the internet, https://www.fda.gov/MedicalDevices/ProductsandMedicalProcedures/ImplantsandProsthetics/BreastImplants/ucm239995.htm.

Geller et al., "Use of an Immunoisolation Device for Cell Transplantation and Tumor Immunotherapy" Annals New York Academy of Sciences, 438-451.

Hu et al., "Biodegradable porous sheet-like scaffolds for soft-tissue engineering using a combined particulate leaching of salt particles and magnetic sugar particles" Journal of Bioscience and Bioengineering 2013, 116(1): 126e131.

International Search Report and Written Opinion, International Appl. No. PCT/EP2018/061513 dated Aug. 10, 2018, 16 pages.

Kong et al., "Rapid mixing of viscous liquids by electrical coiling" Scientific Reports, Feb. 10, 2016, vol. 6, No. 1.

Lang et al., "A Blood-Resistant Surgical Glue for Minimally Invasive Repair of Vessels and Heart Defects" Sci Transl Med. Jan. 8, 2014; 6(218): 218ra6.

Mashak & Rahimi, "Silicone Polymers in Controlled Drug Delivery Systems: A Review" Iranian Polymer Journal 2009, 18(4): 279-295.

Murphy et al., "Salt Fusion: An Approach to Improve Pore Interconnectivity within Tissue Engineering Scaffolds" Tissue Engineering 2002, 8(1): 43-52.

Nie et al., "Microfluidic fabrication of hydrogel-fiber-based 3D constructs utilizing liquid rope-coil effect." 2016 IEEE 29th International Conference on Micro Electro Mechanical Systems (MEMS). Jan. 24, 2016, pp. 207-209.

Phillips, "Photopolymerization" Journal of Photochemistry 1984, 25:79-82.

Qazi et al., "Influence of Surfactants on Sodium Chloride Crystallization in Confinement" Langmuir 2017, 33: 4260-4268.

Ribe et al., "Liquid Rope Coiling" Annu. Rev. Fluid. Mech. 2012, 44:249-66.

Ribe et al., "Multiple coexisting states of liquid rope coiling" J. Fluid Mech. 2006, 555: 275-297.

Sieving et al., "Phase I Study of Ciliary Neurotrophic Factor (CNF) Delivered by Intravitreal Implant of Encapsulated Cell Technology (ECT) Device in Patients With Retinitis Pigmentosa" AVRO Annual Meeting Abstract, May 2005, vol. 46, 531.

Steiert et al. "Capsular contracture by silicone breast implants: possible causes, biocompatibility, and prophylactic strategies" Medical Devices: Evidence and Research 2013, 6: 211-218.

Tran et al., "A new generation of sodium chloride porogen for tissue engineering." Biotechnology and Applied Biochemistry 2011, 58(5): 335-344.

Xu et al., "Bioinspired Microfibers with Embedded Perfusable Helical Channels" Adv. Mater. 2017, 1701664.

Yang et al., "Additive-manufactured polycaprolactone scaffold consisting of innovatively designed microsized spiral struts for hard tissue regeneration" Biofabrication (2017) 9: 015005.

Zhang et al., "Hydrolytically Degradable Hyperbranched PEG-Polyester Adhesive with Low Swelling and Robust Mechanical Properties" Adv. Healthcare Mater. 2015, 4: 2260-2268.

Zhao et al., "Preparation of Microporous Silicone Rubber Membrane with Tunable Pore Size via Solvent Evaporation-Induced Phase Separation" ACS Appl. Mater. Interfaces 2013, 5: 2040-2046.

\* cited by examiner

Macroencapsulation device (a) Monocoque implementation (b) Removable inner pouch implementation

IMPLANTABLE MEDICAL DEVICE

FIELD OF THE INVENTION

The present invention relates to an implantable medical device, and in particular an implantable cell encapsulating device.

BACKGROUND TO THE INVENTION

Current reinforcement of living tissue (for example veins) can be achieved using electrospinning. Electrospinning is problematic as it involves the use of harsh solvents to make a polymer flow, and these solvents can damage living tissue. It is a very time-consuming technique, which if carried out in a surgical setting can potentially damage or kill the cells in the living tissue due to the time required to fabricate an electrospun reinforcing scaffold. In addition, the range of pore sizes and fibre diameter created in an electrospun scaffold are generally limited to a range, which may not be ideal for all tissue ingrowth and structural support applications.

Direct 3d printing of cellular scaffolds are often done by printing rows of straight lines, then on the next layer, repeating at 60 or 90 degree rotation. This leaves many corners and straight lines within the pores. Generally, it is believed cells prefer to thrive on rounded surfaces (as per J. W. C Dunlop et al—A theoretical model for tissue growth in confined geometries, J. Mech Phys Solids 58, 2010)

Alternative cellular scaffolds require casting solid but dissolvable pore generators such as salts, waxes or polymers into a solid polymer matrix. These pore generators must be leeched out, which is time-consuming and potentially leaves residues.

Yang et al (Biofabrication 9 (2017) 015005) describes three-dimensional polycaprolactone scaffolds formed from printed microsized spiral-like struts, and their potential for use in tissue engineering applications. FIGS. 4-6 show the woven structures and the potential of employing wave-like struts having a high wave angle in hard tissue regeneration.

Current commercial cellular encapsulation devices are generally formed by bonding together of multiple layers of pre-fabricated micro-porous membranes (e.g. Geller, Robin L., et al. "Use of an immunoisolation device for cell transplantation and tumor immunotherapy." *Annals of the New York Academy of Sciences* 831.1 (1997): 438-451 and Sieving, P. A., et al. "Phase I study of ciliary neurotrophic factor (CNF) delivered by intravitreal implant of encapsulated cell technology (ECT) device in patients with retinitis pigmentosa." *Investigative Ophthalmology & Visual Science* 46.13 (2005): 531-531) These are formed from planar layers of material and result in a stiff non-contoured, non-compliant device that often do not conform to the area or contours of the implant site.

Capsular fibrosis and contracture are frequent complications after silicone breast implantation (Steiert, A. E., et al. "Capsular contracture by silicone breast implants: possible causes, biocompatibility, and prophylactic strategies." *Medical Devices* (Auckland, NZ) 6 (2013): 211.) Textured surfaces have been shown to reduce the rate of capsular contracture (Barnsley, G P et al. "Textured surface breast implants in the prevention of capsular contracture among breast augmentation patients: a meta-analysis of randomized controlled trials." *Plastic and reconstructive surgery* 117, no. 7 (2006): 2182-2190.), however current processing methods limit the design freedom of this texturing and current textured silicone breast implants have been linked with a rare form of cancer (https://www.fda.gov/MedicalDevices/ProductsandMedicalProcedures/ImplantsandProsthetics/BreastImplants/ucm239995.htm).

It is an object of the invention to overcome at least one of the above-referenced problems.

SUMMARY OF THE INVENTION

The invention broadly provides an implantable medical device comprising a liquid rope coil scaffold. The implant may consist essentially of the scaffold, where the scaffold is the implant and pores in the scaffold may incorporate one or more agents (i.e. drugs, growth factors), or the scaffold may comprise only part of the medical device, for example an implant that is partly or fully covered with a layer of the scaffold. The porosity of the scaffold may be tailored to suit the application, for example a porosity that is tailored to hold and release drug or biological molecules in vivo, a porosity to provide a surface roughness that is conducive to promotion of in-vivo bio-integration (for example vascularisation) or prevention of fibrosis, or a porosity that provides structural strength. The scaffold may be essentially tubular, or may be provided as a planar structure, or may be any shape and can be used to coat, fully or partially any shape or size of medical implant. The use of liquid rope coiling technique to produce a scaffold addresses many of the limitations of the prior art. For example, the process does not require the use of solvents that could damage tissue. In addition, and compared with electrospinning, the process is rapid and can result on a full coat being deposited on a substrate in a matter of minutes. The fact that the nozzle is kept at a distance above the substrate removes any risk of touching and therefore damaging the substrate. This is particularly important if the nozzle is heated which can cause cauterisation of the tissue. Moreover, the use of liquid rope coil scaffolds in implantable medical devices allows the porosity to be tailored to suit many uses, including pore sizes up to the millimetre range to encourage tissue in-growth. These advantages make the liquid rope coil particularly suited to applications which require deposition of materials contain biological agents (including cells) or the deposition of materials onto other biological materials, including tissues and biologically-based substrates.

In a first aspect, the invention provides an implantable medical device comprising a liquid rope coil scaffold.

In one embodiment, the liquid rope coil scaffold is formed from a single polymer filament. It is advantageous to print continuous lines rather than including starts & stops at the beginning and end of lines. This maintains uniformity in the looping sizes. It also prevents 'blobbing' and reduces tendency for the loops to curl in the opposite direction to their previous (this variability in 'handedness' or 'chirality' is particularly visible in FIG. 2).

In one embodiment, the liquid rope coil scaffold is formed from a rapidly curing polymer. This allows for the technique to be used in a surgical setting (e.g. vein graft reinforcement), where the patient may be under general anaesthetic or may be surgically open, leading to vectors for infection. If the rope coil scaffold is to be used to reinforce an ex-vivo biologically-based implant, the less time the implant spends outside the body, the less hypoxic cell damage will occur.

If the scaffold is being printed directly on to the target site, then it minimizes body contact with un-cured monomers. In addition, if the scaffold is being produced outside a surgical setting, the use of a rapidly curing polymer means that the polymer will not have time to 'slump' (i.e. settle due to gravity) which would close off some pores, which makes the process more conducive to a scalable manufacturing process.

In one embodiment, the liquid rope coil scaffold is formed from a photo-curable polymer. Photocurable polymers are of particular interest as they may facilitate easier incorporation of biological therapeutics that can be denatured by significant changes in pH or temperature if they are used for crosslinking.

In one embodiment, the liquid rope coil scaffold is formed from a polymer having high viscosity or a thixotropic polymer. This means that the liquid rope scaffold will be formed by a viscous rope coiling technique, where the coiling frequency decreases strongly with height, and the rope radius is nearly constant because no gravity-induced stretching occurs. This provides greater control of the dimensions and architecture of the rope coil scaffold.

In one embodiment, the implantable medical device consists essentially of the liquid rope coil scaffold. In one embodiment, the implantable medical device is a liquid rope coil scaffold that is shaped for treatment of a tissue defect, for example a bone, cartilage or osteochondral defect. In one embodiment, the porosity of the scaffold is configured to promote bone or cartilage regeneration. In one embodiment, the porosity is configured to mimic natural bone or cartilage morphology. In one embodiment, the implant is shaped to fit snugly within the defect. In one embodiment, an active agent is incorporated into the pores of the scaffold. The active agent may be held passively, or chemically bonded to the filaments of the scaffold. The active agent could be a drug or a biological growth factor, or it could be an agent that mimics the target tissue, for example hydroxyapatite or calcium phosphate in the case of bone implants, or collagen and glycosaminoglycans or chondroitin sulphate in the case of cartilage. The scaffold may be formed from alginate or hyaluronic acid. In one embodiment, the liquid rope coil scaffold may have a bone or collagen biomimetic structure.

In another embodiment, the implantable medical device may comprise an implant that incorporates a liquid rope coil scaffold. In one embodiment, the implant is partially or completely coated with the scaffold. In one embodiment, the implant is coated or covered (partially or completely) with a composite barrier layer comprising a microporous barrier layer and liquid rope coil scaffold layer. Generally, the microporous barrier layer is the inner layer and the liquid rope coil scaffold is the outer layer.

In one embodiment, the implant is an ex-vivo implant, for example vasculature obtained surgically from the same or a different patient. In one embodiment, the implant is a section of vasculature, for example a section of vein or artery, having a tubular coating/sleeve of liquid rope coil scaffold or composite barrier layer. In this instance, the scaffold increases the structural strength of the device. In one embodiment, the section is vasculature is provided a microporous barrier layer defining a lumen, and having a coating/covering of liquid rope coil scaffold.

In one embodiment, the implant is a prosthetic implant (i.e. man made).

In one embodiment, the implant is a hard prosthetic implant (for example a metal or ceramic implant) that includes a layer of liquid rope coil scaffold. Examples include an artificial joint coated with a liquid rope coil scaffold, which can improve surface roughness and help with bio-integration.

In another embodiment, the implant is a soft prosthetic implant that includes a layer of liquid rope coil scaffold. Examples of soft prosthetic implants include silicone implants (i.e. cosmetic surgery implants such as breast or facial implants), drainage or drug delivery devices (catheters) or implantable devices which may be (fully or partially) coated with a liquid rope coil scaffold, where the non-smooth surface of the scaffold helps reduce the instance of fibrosis occurring at the interface of the implant and tissue.

In another embodiment, the implant is a cell-containing implant, for example a pouch, that is partially or fully coated with the liquid rope coil scaffold. In this embodiment, the scaffold helps with the structural integrity of the device, and provides a surface that promotes vascularisation around the device. The cell-containing implant may be defined by a composite barrier layer comprising a microporous barrier layer and a liquid rope coil scaffold layer.

In one embodiment, the surface of the scaffold mimics closely the surface of the implant. In one embodiment, the implant has an irregular shape. For example, ex-vivo vasculature may have an irregular tubular shape, including elliptical sections.

In one embodiment, the liquid rope coil scaffold is formed from silicone. In one embodiment, the liquid rope coil is formed from the same material as the implant. In one embodiment, the liquid rope coil scaffold is formed from a material comprising a polymeric material and an active agent. In one embodiment, the material is a bio-ink and the active agent is a biological material. In one embodiment, the biological material is selected from a peptide, protein, nucleic acid, antibody or antibody fragment, or a cell. In one embodiment, the liquid rope coil scaffold is formed from a bio-ink comprising a polymeric material and a cell. The cell may be chosen depending on the application. In one embodiment, the implantable medical device is a tissue regeneration scaffold, wherein the scaffold is formed from a bio-ink comprising cells configured to promote tissue regeneration.

In another aspect, the invention provides a liquid rope coil scaffold formed from a material comprising a polymeric material and a biologically active agent.

In another aspect, the invention provides a liquid rope coil scaffold formed from a material comprising a polymeric material and a drug.

In another aspect, the invention provides a liquid rope coil scaffold formed from a bio-ink comprising a polymer and a cell.

In another aspect, the invention provides a tissue regeneration scaffold comprising a liquid rope coil scaffold formed from a bio-ink comprising a polymer and a cell.

In another aspect, the invention provides a tissue regeneration scaffold comprising a liquid rope coil scaffold formed from a material comprising a polymer and a biological growth factor.

In another aspect, the invention provides an intratumoral drug delivery device comprising a liquid rope coil scaffold and a chemotherapeutic drug incorporated into the pores of the scaffold.

In another aspect, the invention provides an implantable catheter comprising a coating of liquid rope coil scaffold.

In another aspect, the invention provides a hernia mesh suitable for treatment of a hernia in a mammal, comprising a liquid rope coil scaffold.

In another aspect, the invention provides an implant for implantation into a tissue defect, such as a bone, cartilage or osteochondral defect, the implant comprising a liquid rope coil scaffold that is typically shaped to fit snugly within the implant. In one embodiment, the liquid rope coil scaffold is formed from a material comprising alginate or hyaluronic acid. In one embodiment, the material comprises one or more components selected from the group consisting of: hydroxyapatite; calcium phosphate; chondroitin sulphate; glycosaminoglycans; biological growth factors; or drugs.

In another aspect, the invention provides a method of implanting an implantable medical device into a mammal, the method comprising a step of coating all or part or the implantable medical device with a liquid rope coil scaffold, and implanting the coated implantable medical device into the mammal.

In another aspect, the invention provides a method for treatment of a tissue defect in a mammal, for example a bone, cartilage or osteochondral defect, the method comprising the steps of:

providing an implant according to the invention comprising or consisting essentially of a liquid rope coil scaffold shaped to fit within the implant; and implanting the implant within the defect.

In one embodiment, the liquid rope coil scaffold is shaped to fit snugly within the defect. In one embodiment, the method includes a step of generating a scan (image) of the defect to be printed; using the scan to calculate a 3-D printer toolpath configured to 3-D print a liquid rope coil scaffold conforming to the shape of the defect; and configuring a 3-D printer to print the liquid rope coil scaffold that conforms to the shape of the defect using the 3-D printer toolpath. In one embodiment, the scaffold is directly printed in-vivo.

In one embodiment, the tissue defect is selected from a bone, cartilage or osteochondral defect.

In one embodiment, the liquid rope coil scaffold is formed from a material comprising alginate, hyaluronic acid or methylcellulose. In one embodiment, the material comprises one or more components selected from the group consisting of: hydroxyapatite; calcium phosphate; chondroitin sulphate; glycosaminoglycans; collagen; biological growth factors; or drugs.

In another aspect, the invention provides a method of preparing a section of vasculature for grafting into a mammal, comprising the step of coating the section of vasculature with a liquid rope coil scaffold.

In another aspect, the invention provides a method for performing a body lumen graft in a mammal, the method comprising the steps of:

providing a section of body lumen to be grafted;

coating the section of body lumen with a liquid rope coil scaffold that embraces the body lumen; and grafting the coated section of body lumen into the mammal.

The section of body lumen may be vasculature (venous, arterial, or lymphatic), or another type of body lumen, for example digestive tract, urether, urethra, or the like. The section of body lumen may be mammal to be treated, or a different mammal.

In another aspect, the invention provides a method of implanting a prosthetic implant in a mammal, the method comprising the steps of:

coating the prosthetic implant with a liquid rope coil scaffold; and implanting the coated prosthetic implant into the mammal.

The prosthetic implant may be a hard implant (for example a metal or ceramic implant), or a soft implant, for example a silicone-based implant.

In another aspect, the invention provides a method for treating a disease in a mammal, the method comprising the steps of:

providing a liquid rope coil scaffold containing a therapeutic agent suitable for treatment of the disease; and implanting the coated prosthetic implant into the mammal.

Typically, the therapeutic agent is passively retained within the pores of the scaffold. In another embodiment, the therapeutic agent is chemically attached to the filaments of the scaffold. In one embodiment, the scaffold has a porosity configured for retaining the therapeutic agent prior to implantation and release of the therapeutic agent upon implantation.

In another aspect, the invention provides a method for intratumoral treatment of cancer in a mammal, the method comprising the steps of:

providing a liquid rope coil scaffold containing a therapeutic agent suitable for treatment of the disease; and intratumorally implanting the coated prosthetic implant into a tumour in the mammal.

In one embodiment, the method includes an initial step of surgical re-section of the tumour.

In one embodiment, the liquid rope coil scaffold is directly 3-D printed intratumorally.

In another aspect, the invention provides a method for treatment of a wound in a mammal, the method comprising the steps of:

providing a liquid rope coil scaffold; and implanting the liquid rope coil scaffold in the wound the mammal.

In one embodiment, the liquid rope coil scaffold is directly 3-D printed in the wound.

In another aspect, the invention provides a method for treatment of a hernia in a mammal, the method comprising the steps of:

providing a hernia mesh comprising a liquid rope coil scaffold; and applying the hernia mesh to the hernia in the mammal.

In another aspect, the invention provides a method for treatment of a mammal, the method comprising the steps of:

printing a liquid rope coil scaffold directly on to a target location in the mammal.

The target location may be an organ, bone, tumour, tissue, wound, hernia.

The invention also relates to a method of coating a surface of a medical device comprising the steps of scanning the surface to be coated, using the scan to calculate a 3-D printer toolpath configured to maintain the printing nozzle a constant distance over the surface, and actuating a 3-D printer using the 3-D printer toolpath to print a coating of liquid rope coil on the surface. The scanning may be performed using a single point (one dimensional) measurement laser which is rastered back and forth over the surface measuring profiles along the axis and then rotating and repeating. The measurement data can be used to build a virtual model of the surface, for example in a CAD program. The model can be used to calculate the printer toolpaths which are required to maintain a fixed distance over the surface, while also maintaining a constant linear velocity over the surface.

In another aspect, the invention provides an implantable active agent encapsulating device for implantation in the body, the device comprising a planar pouch having a chamber for encapsulation of active agent defined by a microporous barrier layer, a macroporous strengthening layer, and a port for selective access to the chamber, wherein the macroporous strengthening layer typically comprises a liquid rope coil scaffold.

In one embodiment, the wall of the pouch comprises a laminate of the one or more macroporous strengthening layers and one or more layers of microporous barrier layer.

In one embodiment, the macroporous strengthening layer is sandwiched between at least two layers of microporous barrier layer.

In another embodiment, the macroporous strengthening layer forms an external surface of the pouch suitable for vascularisation.

Thus, in one embodiment, the invention provides an implantable active agent encapsulating device for implantation in the body, the device comprising:
- a pouch having a chamber for encapsulation of active agent defined by a microporous barrier layer, and a port for selective access to the chamber; and
- an external macroporous vascularisation layer substantially covering the microporous barrier layer,
- wherein the macroporous vascularisation layer comprises a liquid rope coil scaffold.

In another aspect, the invention provides an implantable active agent encapsulating device for implantation in the body, the device comprising a planar pouch having a chamber for encapsulation of active agent defined by a microporous barrier layer, a macroporous strengthening layer, and a port for selective access to the chamber,
wherein the chamber comprises a cellular structure that is optionally defined by a cellular framework disposed within the chamber configured to distribute active agent throughout the chamber and minimise thickness variability across the chamber.

In another aspect, the invention provides an implantable active agent encapsulating device for implantation in the body, the device comprising a planar pouch having a chamber for encapsulation of active agent defined by a microporous barrier layer, a macroporous strengthening layer, and a port for selective access to the chamber,
wherein the microporous barrier layer comprises a silicone membrane.

In another aspect, the invention provides implantable active agent encapsulating device for implantation in the body, the device comprising a planar pouch having a chamber for encapsulation of active agent defined by a microporous barrier layer, a macroporous strengthening layer, and a port for selective access to the chamber
wherein the microporous barrier layer comprises a polymer membrane formed by solvent induced phase separation or colloidal templating, combined with particle leaching.

In another aspect, the invention provides for the use of a liquid rope coil scaffold as an implantable scaffold for delivering a therapeutically active agent into the body.

In another aspect, the invention provides a liquid rope coil scaffold suitable for use as an implantable scaffold for regenerative medicine or tissue engineering applications, wherein the pores of the scafoild are gradiated to encourage vascularisation or cell retention as appropriate.

In another, aspect, the invention provides of forming a medical device where the liquid rope coil scaffold comprises of a degradable or non-degradable material impregnated with cells and/or therapeutics.

In another aspect, the invention provides an implantable scaffold comprising a porous liquid rope coil scaffold and cells or a therapeutically active agent entrapped within the pores of the liquid rope coil scaffold.

In another aspect, the invention provides an implantable scaffold comprising a porous liquid rope coil scaffold having a plurality of layers of different porosity. For example, a first layer may have a first porosity, and a second layer may have a second porosity smaller than the first porosity. In one embodiment, the scaffold comprises at least 3, 4, 5 or 6 layers of differing porosity. In one embodiment, the scaffold has a porosity gradient across the scaffold. In one embodiment, the porosity of the layers is gradiated to encourage a first stem cell differentiation in one layer and a second different stem cell differentiation in a second layer.

In one embodiment, the pores of the scaffold is seeded with cells, typically stem cells.

In one embodiment, the pores of the scaffold comprise a porosity gradient configured for cartilage engineering/replacement.

In one embodiment, the liquid rope coil scaffold is biodegradable. In one embodiment, the liquid rope coil scaffold is non-biodegradable.

The invention also relates to a method of regenerating tissue in a mammal comprising a step of implanting an implantable scaffold of the invention into the mammal. The invention also relates to a method of engineering tissue in a mammal comprising a step of implanting an implantable scaffold of the invention into the mammal.

In another aspect, the invention provides for the use of a liquid rope coil scaffold as a microporous barrier layer in an implantable cell encapsulating device.

In another aspect, the invention provides for the use of a porous polymer barrier layer formed by solvent induced phase separation or colloidal templating, combined with particle leaching, as a microporous barrier layer in an implantable cell encapsulating device.

In another aspect, the invention provides an implantable scaffold comprising a microporous liquid rope coil scaffold and a biologically active agent dispersed within the scaffold.

In another aspect, the invention relates to a method of treating a disease in a subject comprising a step of implanting an implantable cell-containing cell encapsulating device into the subject, whereby the cells release a therapeutic factor in-vivo in the subject.

In another aspect, the invention relates to a method of treating diabetes in a subject comprising a step of implanting an implantable a cell-containing cell encapsulating device into the subject, wherein the cells release insulin in-vivo in the subject, and wherein the cells are Islet cells or glucose-stimulated insulin-secreting cells.

In another aspect, the invention provides a method of forming an implantable active agent encapsulating device of the invention in which the macroporous vascularisation layer is adhered to the inner microporous barrier layer, the method comprising the steps of:
- providing a planar pouch comprising a chamber for encapsulation of cells defined by a microporous barrier layer, and a port for selective access to the chamber; and
- printing a liquid rope coil microporous vascularisation layer on the microporous barrier layer.

In another aspect, the invention provides a method of forming an implantable cell encapsulating device of the invention in which the inner pouch is detachable and removable from the external macroporous vascularisation layer, the method comprising the steps of:
- printing a first liquid rope coil macroporous vascularisation layer;
- providing an outer peripheral frame on the first liquid rope coil macroporous vascularisation layer;
- placing a sacrificial layer on an inside face of the first liquid rope coil macroporous vascularisation layer;
- printing a second liquid rope coil macroporous vascularisation layer on the first liquid rope coil macroporous vascularisation layer enclosing the sacrificial layer to form a two-layer construct;

treating the construct to remove the sacrificial layer and provide a hollow liquid rope coil microporous vascularisation pouch; and placing the planar pouch within the hollow liquid rope coil microporous vascularisation pouch.

In one embodiment, the planar pouch is formed by the steps of:

providing a first microporous barrier layer;

placing a support structure comprising an outer peripheral frame and an inner framework configured to help maintain thickness uniformity across the pouch on an inner surface of the microporous barrier layer sheet;

overlying a second microporous barrier layer on the first microporous barrier layer; and sealing the barrier layers to the peripheral frame to provide a planar pouch defined by the peripheral frame and the first and second microporous barrier layers and enclosing the inner framework.

In one embodiment, the liquid rope coil comprises a filament having a thickness of 50-200 μm and a loop size of 1-2 mm.

In one embodiment, the liquid rope coil is formed from a single filament.

In one embodiment, the liquid rope coil scaffold is a silicone liquid rope coil scaffold.

In one embodiment, the planar pouch includes a support structure comprising an outer peripheral frame and an inner framework configured to help maintain thickness uniformity across the pouch.

In one embodiment, the inner framework comprises a plurality of spacing arms configured to distribute cells within the pouch.

In one embodiment, the inner framework comprises a plurality of spacers that provide connection between upper and lower internal faces of the planar pouch at a plurality of positions across the pouch.

In one embodiment, the microporous silicone barrier layer is formed by solvent induced phase separation or colloidal templating, combined with particle leaching, and has an average pore size of less than 10 μm.

In one embodiment, the microporous barrier layer is a silicone based organic polymer.

In one embodiment, the microporous barrier layer is a polydimethylsiloxane (PDMS).

In one embodiment, the microporous barrier layer has an average pore size of 0.2-20 μm.

In one embodiment, the microporous barrier layer comprises a liquid rope coil layer.

In one embodiment, the inner pouch is detachable and removable from the external macroporous vascularisation layer.

In one embodiment, the inner pouch is adhered to the external macroporous vascularisation layer.

In another aspect, the invention relates to composite barrier layer comprising a polymeric lattice layer (for example a polymeric liquid rope coil layer) sandwiched between at least two layers of microporous barrier layer. The composite barrier layer of the invention has a non-planar surface morphology, for example a surface scattered with multiple domed areas (see photo FIG. 7). This 3D membrane surface has a vastly increased surface area, with which improves oxygen and nutrient transfer.

In one embodiment, the composite barrier layer comprises at least two layers of microporous barrier layer (for example, 2, 3, 4, 5, 6, 7, 8, 9, or 10), a liquid rope coil layer, and at least two further layers of microporous barrier layer (for example, at least 2, 3, 4, 5, 6, 7, 8, 9 or 10).

In one embodiment, the microporous barrier layer is an elastomer, for example a siloxane such as PDMS. In one embodiment, the liquid rope coil is an elastomer, for example a siloxane such as PDMS.

The invention also relates to a process for forming a composite barrier layer having non-planar surface topography comprising the steps of:

providing a poragen-containing polymeric layer (i.e. by solvent induced phase separation);

printing a polymer lattice layer on the poragen-containing polymeric membrane; optionally crosslinking the layers; and removing poragen from the polymeric layer by immersion in a suitable solvent to provide the composite barrier layer.

In one embodiment, the composite barrier layer is formed by a process involving the following steps:

combining a solvent and a poragen (for example a crystal such as a salt or a sugar—the solvent may be an aqueous or non-aqueous solvent, preferably water);

optionally adding a polyethylene glycol;

adding a surfactant;

optionally adding a suspended fibre (for example nanocrystalline cellulose);

mixing to provide a first mixture;

combining an elastomer and a suitable solvent (i.e. Hexane, Heptane, Xylene) and mixing to provide a sprayable second mixture;

combining the first and second mixtures in a ratio of 1:1 to 3:1, and ideally about 2:1 to provide a final mixture;

spraying a first layer of the final mixture on a surface;

allowing water and solvent to evaporate from the first layer;

printing a polymeric liquid rope coil layer on the first (or uppermost) layer;

spraying a second layer of the final mixture on the polymeric liquid rope coil layer to provide a composite layered structure;

optionally crosslinking the composite layered structure (i.e. by heating to a temperature sufficient to crosslink the polymer without boiling of the polymer, i.e. 40-150 C, preferably 40-70° C.); and removing poragen from the composite layered structure to provide the composite barrier layer.

In one embodiment, a plurality of first layers are provided prior to the liquid rope coil layer being printed on to the uppermost first layer.

In one embodiment, a plurality of second layers are sprayed on top of the liquid rope coil layer to provide the composite layered structure.

Typically, the poragen is dissolved out of the composite layered structure, for example by immersing the composite layered structure in a suitable solvent (i.e. deionised water) and optionally exposing the layered structure and solvent to ultrasonication.

The liquid rope coil scaffold employed in the products and methods of the invention may be formed from a single filament. The coil size of the rope coil scaffold may be constant, or may be variable. In one embodiment, the coil diameter is about 100 to 5000 microns, preferably about 100-1000 microns. For rope coils that are employed as structural supports for body lumen (e.g. vasculature implants), the rope coil layer typically has a loop size of about 1-3 mm, and preferably about 1.5-2.5 mm. For use in filling defects in hard material such as bone, a loop size of 100-800 microns, preferably about 300-600 microns, is preferable. In one embodiment, a ratio of the filament thickness to the loop size is about X to Y. In one embodiment, the polymer comprises an additive configured to reduce its flowability, and ideally make it non-flowable. Additives/modifiers such as Fumed Silica (at 2-3%) or fine ground Kaolin powder may be employed. Failure to do so can result in the rope coil material slumping/settling such that the pores close.

Other aspects and preferred embodiments of the invention are defined and described in the other claims set out below.

DETAILED DESCRIPTION OF THE INVENTION

Figure 1:
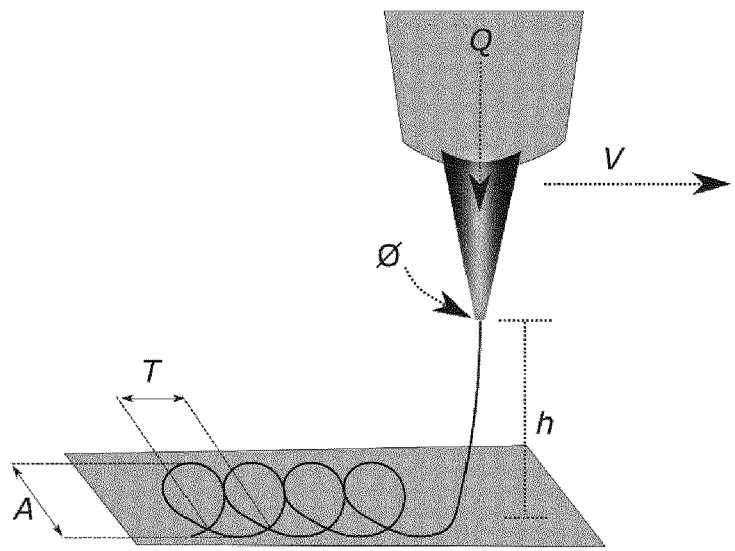
FIG. 1—Parameters that affect the Amplitude (A) and Period (T) of an extruded rope-coil:
Q—Material Flow Ø—Nozzle Diameter (the product of which can be used to calculate the extruded bead length per unit time)
V—Printhead (nozzle) velocity—The ratio of V to bead length per time defines loop shape and period length
h—Nozzle height above substrate—This defines the amplitude of the rope coil loops (at certain fixed values of Q, V and Ø, the loop A will be linearly proportional to h).

All publications, patents, patent applications and other references mentioned herein are hereby incorporated by reference in their entireties for all purposes as if each individual publication, patent or patent application were specifically and individually indicated to be incorporated by reference and the content thereof recited in full.
Definitions and General Preferences
Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising,"are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies. In one embodiment, the disease is treatable by autologous, allogenic or xenogenic transplantation of cells into the body contained within a cell encapsulation device. An example of such a disease is diabetes, where insulin-producing cells (i.e.

islet cells) are transplanted into the body. In one embodiment, the islet cells are pancreatic beta cells.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy". In one embodiment, the treatment is therapeutic cell transplantation, for example therapeutic islet transplantation for treatment of diabetes or other metabolic disease characterised by dysregulated insulin production.

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an "effective amount or a therapeutically effective amount" of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

In this specification, the term "liquid rope coil scaffold" should be understood to mean a macroporous scaffold formed from a polymer (i.e. an elastomer or hydrogel, optionally comprising an additional agent such as a therapeutic agent, additive or filler) by liquid rope coil methodology. The liquid rope coil methodology is described in Brun et al (Phys. Rev. Lett. 114, 174501 (2015) and U.S. Pat. No. 9,079,337), and takes advantage of the phenomenon where a viscous jet of fluid will curl and loop repeatedly and predictably (termed "the liquid rope coil effect" or "viscous thread instability"). In one embodiment, the liquid rope coil is generated by a viscous regime of rope coiling (i.e. viscous rope coiling), where both gravity and inertia are negligible and the net viscous force on each fluid element is zero. The coiling frequency decreases strongly with height, and the rope radius is nearly constant because no gravity-induced stretching occurs (Ribe et al—J. Fluid Mech. (2006), vol. 555). To achieve viscous rope coiling, the polymer employed is typically a Newtonian fluid of sufficiently high viscosity that the material will not flow or self level due to gravity, nor change resting form without an application of shear. The polymer may be thixotropic. In one embodiment, the elastomer is silicone, or a silicone based organic polymer. In one embodiment, the silicone based organic polymer is a siloxane, optionally selected from polydimethylsiloxane (PDMS). In one embodiment, the liquid rope coil scaffold is formed from a hydrogel such as alginate, methylated hyaluronic acid, a polycaprolactone (PCL) or a polyurethane which has been made thixotropic In one embodiment, the scaffold is made from a single continuous filament. The polymer may also be formed from monomers or pre-polymers that are crosslinked to form a polymer. In one embodiment, the filament has a thickness of 50-200 µm, 75-150 µm, 100-200 µm, 50-100 µm or 100-150 µm. In one embodiment, the liquid rope coil scaffold has a thickness of 100 to 1000 µm, typically between 150 and 600 µm. In one embodiment, the rope coil layer is 1 to 5 coils in thickness, and preferably 1 coil in thickness. In one embodiment, the coil diameter is about 100 to 5000 microns, preferably about 100-1000 microns. For rope coils that are employed as structural supports for body lumen (e.g. vasculature implants), the rope coil layer typically has a loop size of about 1-3 mm, and preferably about 1.5-2.5 mm. For use in filling defects in hard material such as bone, a loop size of 100-800 microns, preferably about 300-600 microns, is preferable. In one embodiment, a ratio of the filament thickness to the loop size is about 1:2 to about 1:25, or any ratio in between, for example 1:2 to 1:10, 1:10 to 1:25, or 1:5 to 1:10. In one embodiment, the liquid rope coil scaffold had variable coil size (i.e variable pore size architecture). This provides for scaffolds having different porosity at different positions on the scaffold. For example, the scaffold may have bigger pores towards the periphery and smaller pores towards the centre. In one embodiment, the polymer comprises an additive configured to reduce its flowability, and ideally make it non-flowable. Additives/modifiers such as Fumed Silica (at 2-3%) or fine ground Kaolin powder may be employed. Failure to do so can result in the rope coil material slumping/settling such that the pores close. In one embodiment, the polymer is a rapidly curing polymer. In one embodiment, the polymer is a photo-curable polymer. In one embodiment, the liquid rope coil scaffold is formed from a polymer having high viscosity or a thixotropic polymer.

In this specification, the term "rapidly curing polymer" should be understood to mean a polymer configured to cure in less than 60 minutes, and preferably within less than 50, 40, 30 or 20 minutes. This is especially applicable for scaffolds that are printed in-vivo, and also facilitates manufacturing scaffolds in a high-throughput manner.

In this specification, the term "photo-curable polymer" refers to a polymer that cures (hardens) as a result of cross-linking when exposed to light, often light in the ultraviolet or visible region of the electromagnetic spectrum. In one embodiment, the photo-curable polymer includes a photoinitiator such as a free-radical photo-initiator. Photo-curable polymers are described in: Reichmanis et al (Chem. Mater. (2014) 26: 533-548); Philips (Journal of Photopolymerisation (1984) 25: 79-82). Lang et al. Sci Trans Med 2014 6: pp 218, U.S. Pat. No. 9,724,447B2—Hydrophobic tissue adhesives; and Zhang, Hong, et al. "Hydrolytically Degradable Hyperbranched PEG-Polyester Adhesive with Low Swelling and Robust Mechanical Properties." Advanced healthcare materials 4.15 (2015): 2260-2268.

In this specification, the term "high viscosity" as applied to a polymer means a Newtonian fluid of sufficiently high viscosity that the material will not flow or self-level due to gravity, nor change resting form without an application of shear. The polymer may be thixotropic. Examples of high-viscosity polymers suitable for forming liquid rope coil scaffolds include: NuSil Med4820 High consistency silicone; NuSil Med4840 High consistency silicone; Dow Corning Sylgard 184 with an added 2%/wt fumed silica (Silicone); Polycaprolactone (PCL) Thermoplastic heated to 60° C.; Hydrogel composed of 2% Hyaluronic Acid, 2% K-Carrageenan and 2% Fumed Silica (with 94% Water); and Hydrogel of Sodium Alginate 3% with Xanthan Gum 0.5% with D.I. Water 96.5% (followed by polymerisation by immersion (post 3d-print) in a bath of 2% Calcium Chloride & Water).

In this specification, the term "thixotropic" as applied to a polymer means that when shear stress is applied to the polymer (for example, during extrusion), the storage modulus (G') reduces, the tan δ increases and the overall viscosity reduces.

In this specification, the term "implantable medical device" or "implantable scaffold" should be understood to mean a medical device comprising (or consisting essentially of) a liquid rope coil structure, that is configured for implantation into the body. The implantable medical device is biocompatible (i.e. can be implanted into the body without causing a substantial host immune response), and is typically sterile. The term includes scaffolds for tissue engineering/tissue regeneration, various types of implants including hard implants made from metal or ceramic materials (i.e. orthopaedic implants and stents), soft implants such as inflatable balloons, cosmetic surgery implants and implantable, drainage or delivery devices such as catheters, ex-vivo implants such as vein grafts, drug delivery implants configured to release therapeutic agent in-vivo, and cell delivery devices (i.e. implantable pouches). The implantable medical device may be employed for any therapeutic purpose, including tissue regeneration, tissue replacement, tissue engineering and/or delivery of therapeutically active agents into the body. In one embodiment, the scaffold is used for the purpose of gradual release of therapeutically active agents in the body. In one embodiment, the device is a tissue regeneration scaffold, for use in regenerating a tissue selected from skin, organs, bone, vasculature, cartilage, muscle.

When the device contains a therapeutically active agent, it is generally contained within the liquid rope coil scaffold, ideally retained within the porous 3-D network of the scaffold. In one embodiment, the therapeutically active agent is chemically or physically attached to the filament(s) of the liquid rope coil scaffold. Methods of attaching therapeutically active agents to a polymeric filament are described in "A comprehensive review of Silicone polymers in drug delivery" (Mashak and Rahimi (Iranian Polymer Journal 18 (4), 2009, 279-295)).

As used herein, the term "hard implant" refers to an implant formed of a hard material, such as metal or a ceramic material, and includes orthopaedic implants. The use of a coating of liquid rope coil scaffold on the implant generates a surface roughness on the impant in-vivo which aids in bio-integration of the implant in-vivo. As used herein, the term "soft implant" refers to an implant formed of a soft material, such as a silicone breast implant or other cosmetic implants, or soft implantable medical devices such as silicone catheters, where the liquid rope coil scaffold on the implant helps prevent fibrosis occurring at the interface of the implant and tissue.

In this specification, the term "therapeutically active agent" should be understood to mean biological and non-biological agents that are therapeutically active in mammals, such as drugs, and biological molecules such as cells, protein, peptides, sugars, and nucleic acids, and conjugates of drugs and biological molecules such as antibody drug conjugates. In one embodiment, the biologically active agent is a nucleic acid selected from DNA, RNA, mRNA, tRNA, shRNA, siRNA, gRNA. In one embodiment, the biologically active agent is a therapeutic factor selected from growth factors, proangiogenic factors, insulin, antibodies, antibody fragments, cytokines, interleukins, interferons, biopharmaceutical products, proteins, nucleic acids. Examples of proangiogenic factors include VEGF, FGF, HGF, NPR-1, PDGF, PLGF, and TGF-β. In one embodiment, the therapeutically active agent is a pharmaceutical. The term includes molecules that assist in tissue and bone regeneration, including calcium phosphate, hydroxyapatite, glycosaminoglycans, chondroitin sulphate, collagen, and extracellular matrix (ECM).

In this specification, the term "cells" should be understood to mean any type of eukaryotic or prokaryotic cell, including for example, pancreatic cells, pancreatic Islets, smooth muscle cells, epithelial cells, endothelial cells, progenitor cells, mesenchymal stem cells, antibody producing cells, stem cells, adult stem cells or human or non-human origin. The cells may be wild-type cells, or they may be cells that are genetically engineered. The cells may be obtained from the patient undergoing therapy (autologous cell implantation) or they may be obtained from a different person (allogenic cell implantation) or another species (xenogenic cell implantation). Generally, the cells are living cells. In one embodiment, the cells are insulin-producing cells. Cells may be obtained from tissue of the patient or donors or from cell depositories or research Institutions.

In this specification, the term "active agent" refers to a cell or a part thereof, or a therapeutically active agent.

In this specification, the term "body lumen" refers to vasculature such as arteries, veins, and lymphatic vessels, and other vessels in the mammalian body such as a gastrointestinal tract, ureter, and urethra. In a preferred embodiment, the body lumen is selected from an artery and vein.

In this specification, the term "tissue defect" refers to hard tissue defects and soft tissue defects. Examples of hard tissue defects include bone, cartilage and osteochondral defects. Examples of soft tissue defects include connective tissue disease, chronic wounds, diabetic wounds, sores, impact injuries.

In this specification, the term "implantable cell encapsulating device" should be understood to mean a device configured to hold cells and be implanted into the body, where the cells are retained within the device in the body. Such devices are known from the literature and are described in for example U.S. Pat. No. 5,545,223, 8,129, 182, 9,132,226 and 5,585,613. Generally, the device is configured to keep the cells separate from the host tissue, and especially the host immune response. This is generally achieved by the barrier material of the pouch, which is ideally microporous to retain the cells within the device, keep host immune cells out of the pouch, but allow diffusion of gases and nutrients for maintaining the viability of the cells. In one embodiment, the device has a substantially planar structure. In one embodiment, the device has thickness (distance from one major surface to another major surface) of less than 5 mm, 4 mm, 3 mm, 2 mm or 1 mm, and ideally less than 0.8 mm, 0.6 mm or 0.5 mm. In one embodiment, the device has a substantially uniform thickness. In one embodiment, the device is configured for implantation in the Omentum or sub-abdominally. In one embodiment, the device a maximum length (along a major surface) of 1-20 cm, 3-20 cm, 5-20 cm, 10-20 cm, 1-15 cm, 3-15 cm, 5-15 cm, 10-15 cm. In one embodiment, the device a width (across a major surface at its widest point) of 1-15 cm, 3-15 cm, 5-15 cm, 1-10 cm, 3-10 cm, 5-10 cm. In one embodiment, the device has curved ends and typically has a curved waist section. In one embodiment, the device comprises immune-suppressing drugs which are released from the device in-vivo and serve to suppress the immune response.

In this specification, the term "a chamber for encapsulation" should be understood to mean an enclosed chamber configured to hold cells. The chamber is defined by a microporous barrier layer, and ideally comprises a cellular structure typically configured to distribute cells across the chamber and optionally minimise thickness variability across the chamber. In one embodiment, the cellular structure is defined by a structural framework disposed in the chamber. In one embodiment, the chamber is defined by two planar sheets of microporous barrier layer which are sealed at their periphery to form the chamber for encapsulation of the cells. In one embodiment, the cellular framework is sandwiched between the sheets of microporous barrier layer, and the cellular framework defines the thickness (height) of the chamber across the major surface of the chamber to minimise thickness variations across the device. Variations in thickness of the device (bulging) results in cells in the bulging parts of the device being distanced from a vascular oxygen supply and consequent oxygen starvation. The cellular structure serves to minimise thickness variations across the device and inhibit or prevent bulging.

In this specification, the term "cellular structure" should be understood to mean that the chamber comprises a plurality of interconnected chambers (cells) which divide the chamber into a plurality of smaller sub-chambers, generally at least 5, 10, 12, 14 or 16 sub-chambers, thereby preventing or inhibiting bulging in the pouch and helping minimise thickness variations across the device. The chambers are interconnected to allow cells to be added to the device through a single port and be distributed substantially evenly throughout the cellular structure. In one embodiment, the cellular structure is defined by a cellular framework (inner framework), typically having a series of baffles configured to distribute cells within the pouch and help maintain height/depth uniformity across the pouch, such that substantial bulging of the pouch is avoided. In one embodiment, the cellular framework has a branched structure that defines channels and/or cells within the pouch for even distribution of cells within the pouch. The cellular framework also typically has a substantially uniform height, so as to help maintain height/depth uniformity across the pouch. In one embodiment, the cellular framework has a height of about 0.5 to 5 mm, 0.5 to 2.0 mm and ideally about 0.5 to 1.5 mm. In one embodiment, the cellular framework is formed from an elastomer or polymer, for example silicone or a silicone based organic polymer. In one embodiment, the silicone based organic polymer is a siloxane, optionally selected from polydimethylsiloxane (PDMS) and in one embodiment, the polymer is a polyurethane or an acrylate. In one embodiment, the polymer is a reducing agent such as polymethylhydrosiloxane (PMHS). In one embodiment, the framework is formed from a gas permeable contact lens material, for example polymethylmethacrylate (PMMA). In one embodiment, the cellular framework is produced by 3-D printing. In one embodiment, the microporous barrier layer is attached to the cellular framework. In another embodiment, the cellular structure is defined by the microporous barrier layers being bonded together to form a chamber comprising a cellular structure (similar to an ice-making bag). In another embodiment, the cellular structure is defined by the opposed inner membranes being connected to each other at a plurality of positions across the planar pouch. Spacers may be provided to provide connection between the opposed inner membranes.

In this specification, the term "microporous barrier layer" should be understood to mean a wall that defines a chamber or lumen in the body (for example a chamber for encapsulation of cells, or a lumen for blood) and which has suitable porosity to allow diffusion of gases and certain nutrients yet prevent cells within the chamber or lumen exiting the chamber or lumen. The microporous barrier layer is preferably an immunobarrier, which means that it prevents host immune cells entering the chamber or lumen. In one embodiment, the microporous barrier layer is formed from a polymer, for example an elastomer, and ideally a viscoelastic elastomer. The microporous barrier layer typically comprises porosity generated using a porogen. In one embodiment, the microporous barrier layer comprises silicone. In one embodiment, the microporous barrier layer is formed from a silicone-based organic polymer. In one embodiment, the silicone-based organic polymer is a siloxane, optionally selected from polydimethylsiloxane (PDMS) and in one embodiment, the microporous barrier layer is selected from a reducing agent such as polymethylhydrosiloxane (PMHS). In one embodiment, the microporous barrier layer is selected from a polyurethane or an acrylate. In one embodiment, the microporous barrier layer is formed from a gas permeable contact lens material, for example polymethylmethacrylate (PMMA). In one embodiment, the microporous barrier layer is formed by a method selected from solvent induced phase separation, colloidal templating, particle leaching, or a combination thereof. In one embodiment, the microporous barrier layer is formed from solvent induced phase separation or colloidal templating, combined with particle leaching. In one embodiment, the microporous barrier layer has a thickness of less than 100 µm, 90 µm, 80 µm, 70 µm, 60 µm or 50 µm, as determined by Laser Displacement Measurement or profilometry. In one embodiment, the microporous barrier layer has an average pore size of less than about 20 µm, 15 µm or 10 µm. In one embodiment, the microporous barrier layer has an average pore size of about 0.2-10 µm, 2-10 µm, 4-10 µm, 6-10 µm or 8-10 µm as determined by Mercury Intrusion Porosimetry. In one embodiment, the microporous barrier layer has a porosity of 50-70% and preferably 40-60% as determined by Mercury Intrusion Porosimetry.

In this specification, the term "solvent induced phase separation" or "SIPS" refers to a known process for producing porous membranes in which surfactant is used to disperse two immiscible substances, for example a mix of silicone rubber monomer, a crosslinking agent, and a wax porogen, which are combined with a suitable solvent. When the mixture is formed into a membrane, for example by spray deposition or casting, the solvent is removed in a controlled manner. The immiscible substances coalesce to form bubbles of fluid, where the size of the bubbles are controlled by the speed and manner of solvent removal, along with the type and quantity of surfactant employed. Following crosslinking (vulcanisation) of the silicone, the pore generating material (porogen) is removed by washing the membrane with a suitable solvent. Multiple pore generators and polymers may be used. Surfactants may also be separated from the mixture before, after or at the same time as the pore generator. The process is described in detail in Zhao et al (ACS Appl. Mater. Interfaces 2013, 5, 2040-2046).

In this specification, the term "colloidal templating" refers to a known technique which is similar to SIPS, but instead of using a poragen which is mutually dissolved with a polymer in solvent, the poragen is also immiscible with the solvent, so an emulsion of the two substances is created instead. An example of a poragen in this case is water. The pore size of the final membrane is defined by the surfactant used, and the method/duration of mechanical mixing. Subsequent removal of the liquid phase of poragen can be done via freeze-drying or evaporation. Colloidal templating using crystals for porous materials is described in in a review by Valev (Current Opinion in Colloid & Interface Science Volume 5, Issues 1-2, March 2000, pp 56-63).

In this specification, the term "particle leaching" refers to a known technique that relies on using pore generating materials which are pre-formed at a fixed and known size before being added to the polymer/solvent mix. An example of a poragen in this case can be calcium alginate microspheres or salt crystals. These particles are removed after polymerisation of the membrane, via washing or dissolving. When a sufficient quantity of these particles are added to the polymer mix (termed percolation threshold), then full permeability can be achieved in the membrane. Murphy et al discuss the concept of salt leeching for tissue engineering (Tissue Engineering. July 2004, 8(1): 43-52).

In this specification, the term "porous polymer barrier layer formed by solvent induced phase separation or colloidal templating, combined with particle leaching." should be understood to mean a microporous barrier layer formed by a combination of solvent induced phase separation (SIPS) or colloidal templating, combined with particle leaching. The leached particle can be formed by crystal nucleation and growth, whereby a (super)saturated solution of water and a particle such as salt, sugar or a water soluble polymer such as PEG or PVA (or a combination in the case of co-crystalisation), are prepared and mixed as per colloidal templating. After being deposited and the solvent removed, the water is typically also evaporated, forcing the particle to recrystallise. Tran et al (Biotechnol Appl Biochem. 2011 September-October; 58(5):335-44) discuss the process of dissolved salt crystal nucleation resulting in a narrower distribution of crystal size when compared to adding solid crystals. Hu et al (Journal of Bioscience and Bioengineering Volume 116, Issue 1, July 2013, Pages 126-131) discuss the concept of creating membranes with salt and sugar in combination. Qazi et al. (Langmuir, 2017, 33 (17), pp 4260-4268) discuss the influence of surfactants on sodium chloride crystal growth. The porosity in the barrier layer may be tailored using various process parameters, including speed and manner of solvent removal, the choice of surfactant, and the choice of particulate poragen. Also, the deposited layer thickness plays a significant role in defining the size and homogenisation of the nucleation or agglomeration. Particularly with crystal nucleation, it is preferable to deposit a thin layer (for example by aerosol electrostatic dispersion spraying a layer of <10 μm) on to a warm plate and evaporating the solvent and water before depositing the next layer. The use of SIPS or colloidal templating, combined with particle leaching, has been found to allow the amount of poragen to be reduced compared with use of SIPS or colloidal templating on its own, which increases the structural integrity of the barrier layer while maintaining excellent porosity. In one embodiment, the weight ratio of poragen to polymer ratio employed is less than 0.66, 0.60, 0.55, 0.50, 0.45, or 0.40.

In this specification, the term "poragen" should be understood to mean a material that is added to the polymer during the formation of the barrier layer and is subsequently removed during or after formation of the barrier layer, and ideally after polymerisation of the barrier layer. The poragen may be solid or fluid. In one embodiment, the poragen is a microparticle or a crystal, for example a salt or sugar crystal. In one embodiment, the poragen is wax or a solvent such as water. In one embodiment, the poragen has an average diameter of 2-20 μm.

In this specification, the term "macroporous strengthening layer" should be understood to mean a layer that improves the structural integrity of the microporous barrier layer. The macroporous layer is generally a liquid rope coil scaffold, and may be an external layer (in which case it also functions as a vascularisation layer), or it may be embedded in layers of microporous barrier layer. Increased vascularisation has the benefit of increasing the transport of oxygen and other nutrients to the cells in the pouch. Biologically active molecules or cells can also be attached to, or entrapped within, the macroporous vascularisation layer. The cells may be pro-angiogenic cells. The molecules may be pro-angiogenic molecules, for example VEGF, FGF, HGF, NPR-1, PDGF, PLGF, or TGF-β. In one embodiment, the macroporous layer is biodegradable.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

FIG. 1 illustrates a liquid rope coil being applied to a substrate. The parameters that affect the Amplitude (A) and Period (T) of an extruded liquid ropecoil are:

Q—Material Flow Ø—Nozzle Diameter (the product of which can be used to calculate the extruded bead length per unit time)

V—Printhead (nozzle) velocity—The ratio of V to bead length per time defines loop shape and period length h—Nozzle height above substrate—This defines the amplitude of the rope coil loops (at certain fixed values of Q, V and Ø, the loop A will be linearly proportional to h).

Figure 2:
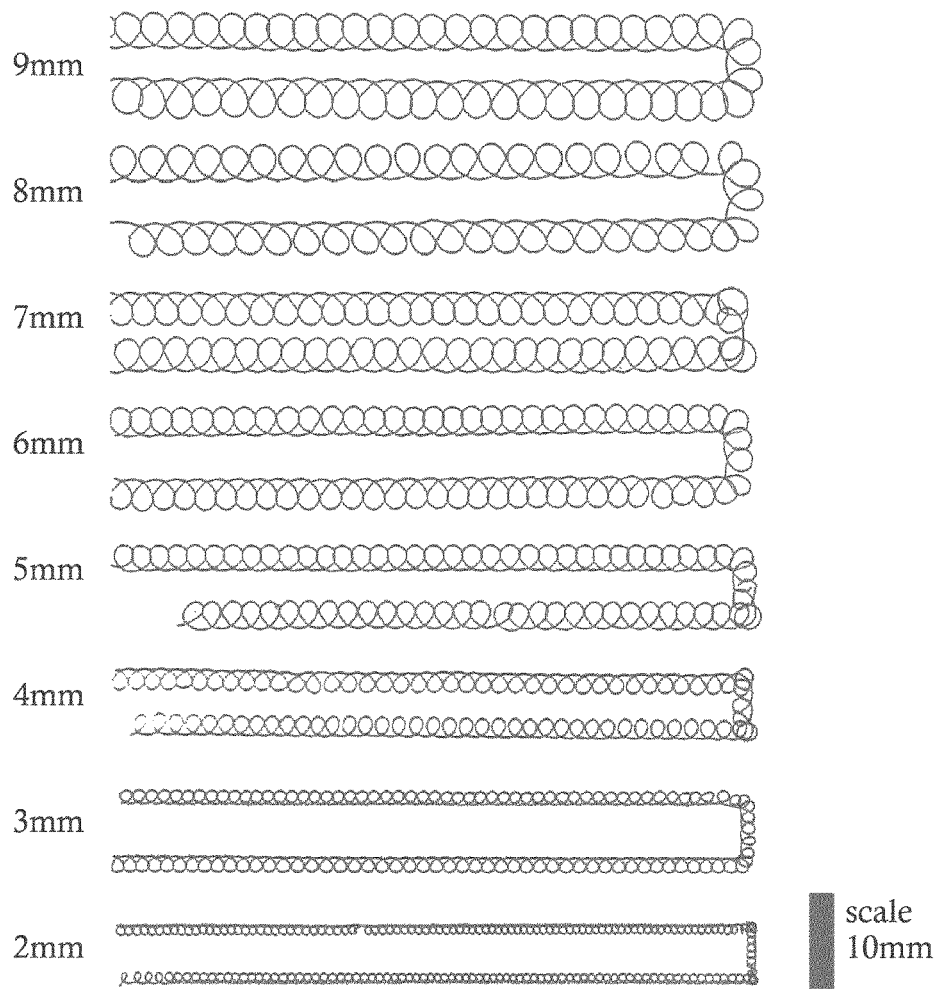
FIG. 2—Example of resulting printed loop sizes when holding Q, V and Ø fixed, and varying only h.
In this case the Q=96 µl/min, V=600 mm/min, Ø=220 µm, and material=NuSil MED4820.

FIG. 2 illustrates examples of resulting printed loop sizes when holding Q, V and Ø fixed, and varying only h.

In this case the Q=140 μl/min, V=600 mm/min, Ø=220 μm, and material=NuSil MED4820.

Figure 3:
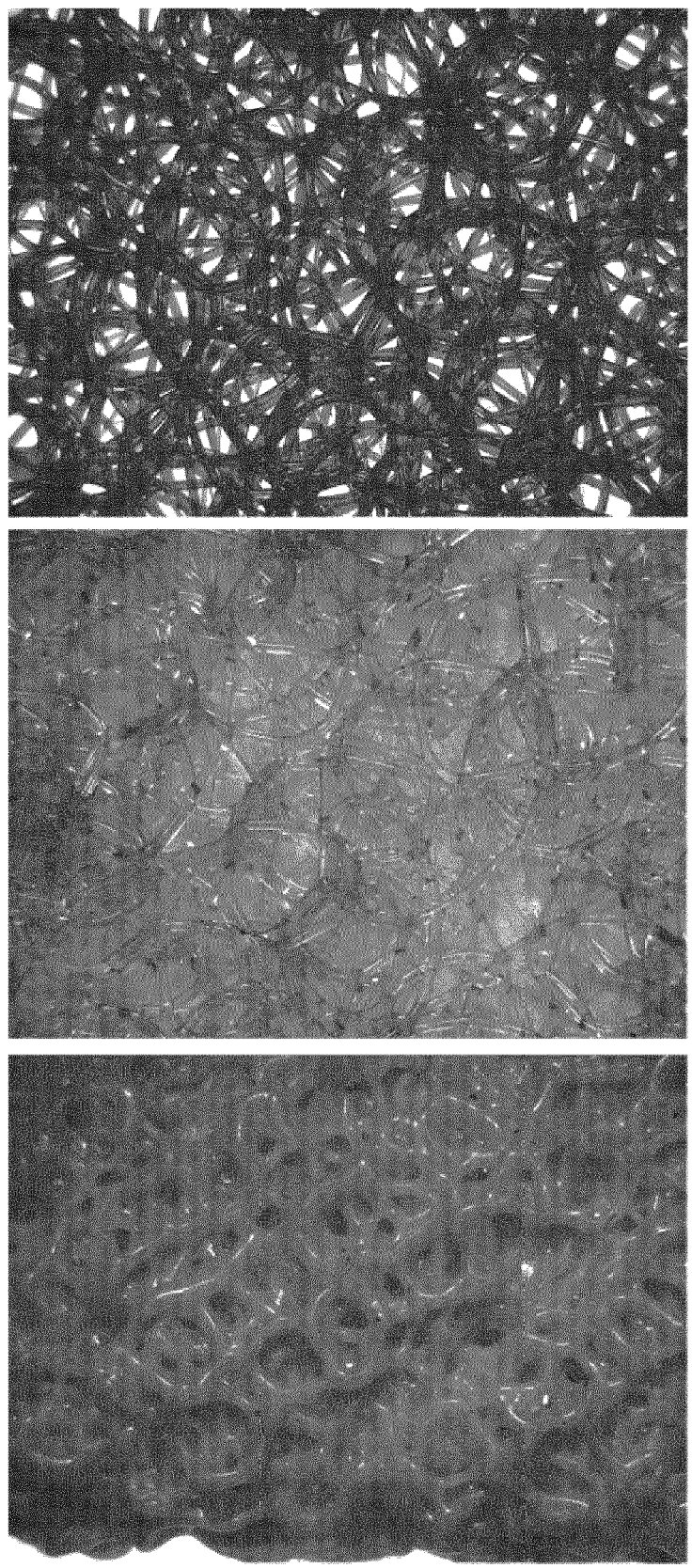
FIG. 3—(a) Magnified image of multiple layers of NuSil MED4820 extruded, each layer extruded 15° clockwise to the previous, with potential use as a cellular scaffold. Extruded bead diameter is 200 µm
(b) NuSil MED 4840 extruded on to a microporous silicone membrane, which functions as a reinforcement and vascularisation accentuator
(c) Mineral filled hydrogel rope coil layer, where the coils are partially allowed to slump. The resulting porous material has a similarity morphology to the trabecular structure of bone.

FIG. 3 is a magnified image of multiple layers of NuSil MED4820 extruded liquid rope coil layer, each layer extruded 15° clockwise to the previous, with potential use as a cellular scaffold. Extruded bead diameter is 200 μm (b) NuSil MED 4840 extruded on to a microporous silicone membrane, which functions as a reinforcement and vascularisation accentuator (c) Mineral filled hydrogel rope coil layer, where the coils are partially allowed to slump. The resulting porous material has a similarity morphology to the trabecular structure of bone.

Figure 4:
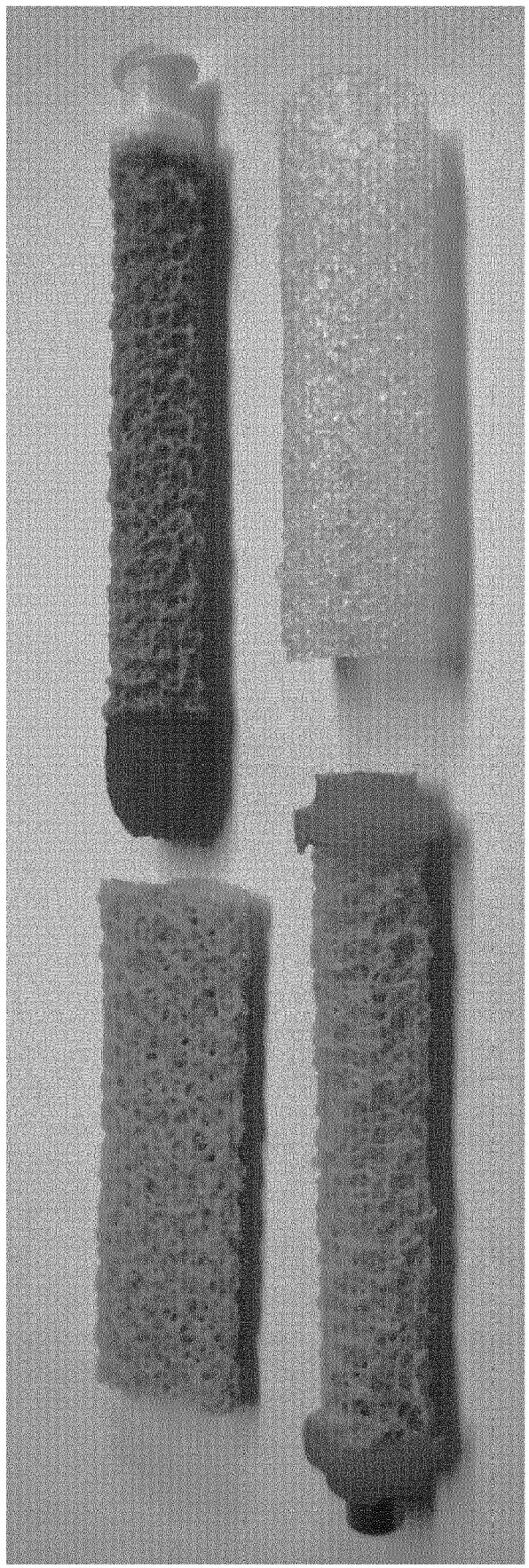
FIG. 4—Four examples of rope coil structures which have been extruded in a tubular form (elliptical and round cross section).
Figure 5:
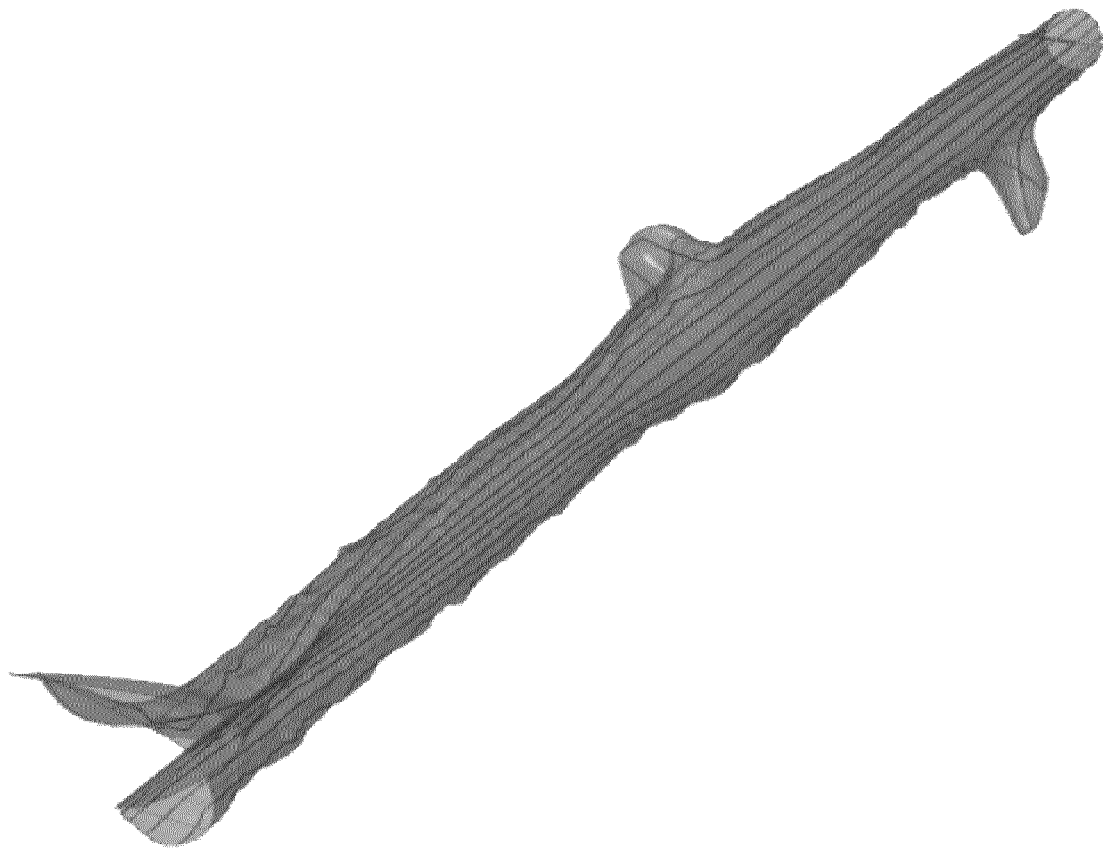
FIG. 5—An example of a reconstruction of a scanned blood vessel.

FIG. 4 illustrates four examples of rope coil structures which have been extruded in a tubular form (elliptical and round cross section), and FIG. 5 is an example of a reconstruction of a scanned blood vessel.

Figure 6:
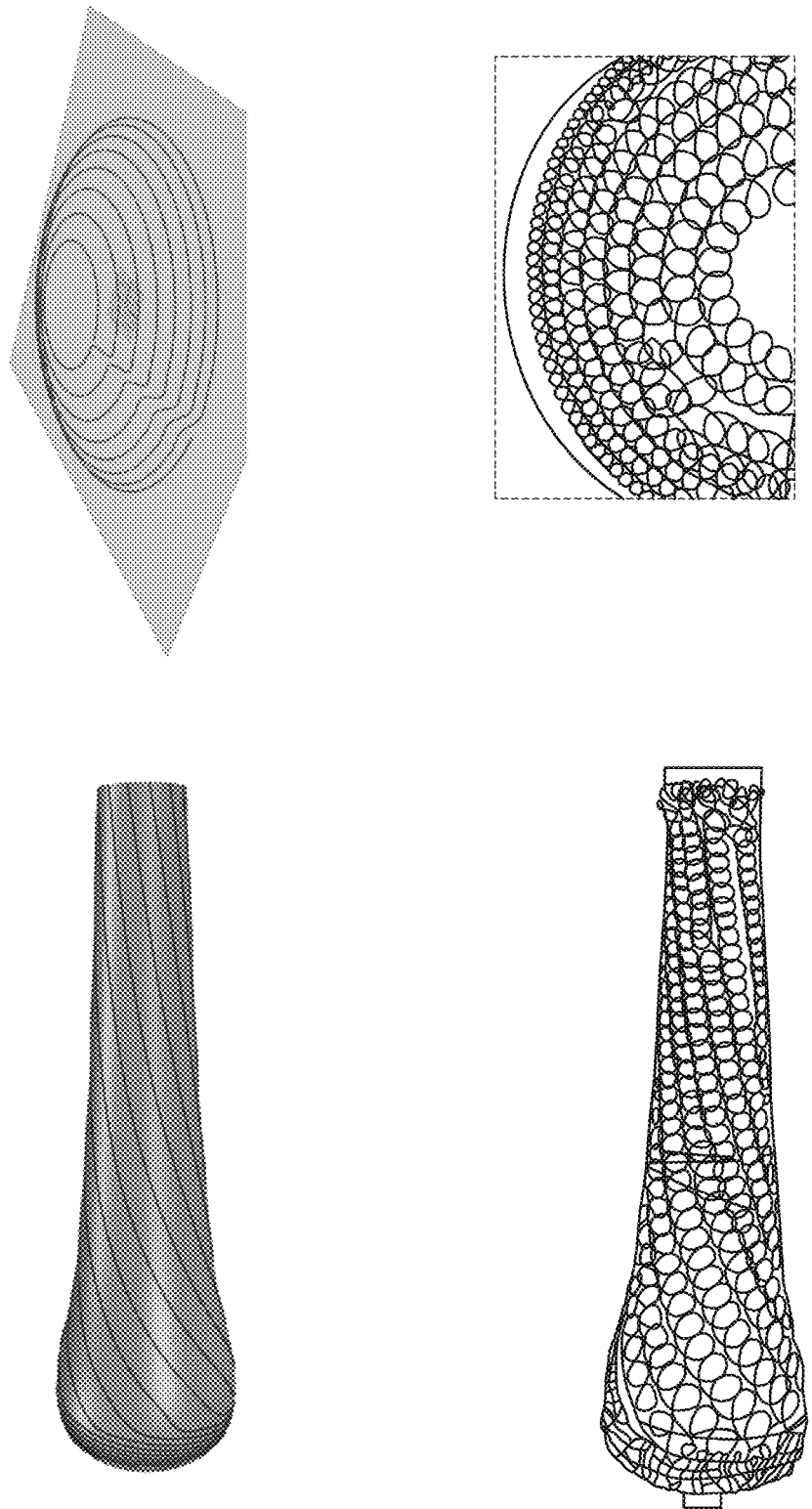
FIG. 6—(a) A non-uniform (varying axial diameter) mandrel form with 13 wrapped helical toolpaths around the surface
(b) A printed rope coil layer on top of the mandrel structure of (a), where the amplitude of the coils are increased in proportion to the diameter of the mandrel, such that the loops just touch each other along the entire surface.
(c) A 3D printer toolpath of concentric rings where the distance between each ring and the next decreases, in proportion to the height of each ring from the substrate
(d) the resulting extruded rope-coil from (c) where the inner most circle has the largest loop amplitude, and outermost the smallest. This structure (when stacked in multiple layers) mimics the decreasing porosity of a planar cross section of bone.

FIG. 6(*a*) a non-uniform (varying axial diameter) mandrel form with 13 wrapped helical toolpaths around the surface. FIG. 6(*b*) shows a printed rope coil layer on top of the mandrel structure of 6(*a*), where the amplitude of the coils are increased in proportion to the diameter of the mandrel, such that the loops just touch each other along the entire surface. FIG. 6(*c*) shows 3D printer toolpath of concentric rings where the distance between each ring and the next decreases, in proportion to the height of each ring from the substrate. FIG. 6(*d*) shows the resulting extruded rope-coil from (c) where the inner most circle has the largest loop amplitude, and outermost the smallest. This structure (when stacked in multiple layers) mimics the decreasing porosity of a planar cross section of bone.

The extruded material can be a gel such as alginate or hyaluronic acid, filled with a mineral such as hydroxyapatite or calcium phosphate. By rope coiling such material in a structure like above, bone-grafts can be created with a biomimetic structure. An example of a bone like structure being extruded on a non-uniform (elliptical cross section) tubular mandrel is shown in FIG. 4. This technique can be used with ex-vivo implants, for example vasculature employed in vein and artery grafts.

Soft materials can be extruded on to an existing medical device such as a metal or ceramic bone implant, which can improve surface roughness, to help bio-integration.

This metal or ceramic implant can be irregularly shaped. The object shape must first be scanned/digitised (either with a 1-dimensional laser at specific points, or 2-dimensional profilometer rastered along the length of the implant). 3D printer Toolpaths can be calculated which maintain a constant distance over the substrate, and a constant linear surface velocity over the substrate. This will result in a constant (and specifiable) loops size being printed on the substrate. A soft material (such as a rapid cross-linking biocompatible elastomer) can be extruded in a rope coil fashion, over the surface of a biological vein graft, before its implantation. This would serve to improve the mechanical properties and preventing kinking, while encouraging new vessel ingrowth around the graft. FIG. 3 is a close-up image of a silicone liquid rope coil reinforcing scaffold. FIG. 5 is a scanned virtual image of an irregular tubular, in this case a section of a vein, which is employed to generate a 3-D printer toolpath that is used to 3-D print a liquid rope coil scaffold coating on the vein.

A Silicone can be extruded in a rope coil fashion over the entire surface of a silicone implant, such as a breast or facial implant or catheter. The non-uniform & non-smooth can help to reduce the instance of fibrosis occurring at the interface of the implant and tissue. The catalyst/stimulus for crosslinking could include chemical crosslinking, thermal-crosslinking, and photo-curing.

As well as the examples above, which concern ex vivo applications of rope coiling, biomaterials could be directly deposited onto soft and hard tissues in vivo using rope coiling techniques to produce porous architectures. Applications could include depositing materials into superficial wounds (performing as a tissue regenerating agent or a dressing that could be used in conjunction with vacuum assisted wound closure), direct deposition of material into bone and cartilage defects, deposition of drug depots/wafers in the treatment of cancer post surgical resection (e.g. glioblastoma), deposition of a hernia mesh in situ. These applications may require in some instances scanning or some form of visualisation of the underlying tissue or wound bed prior to material deposition.

Figure 7:
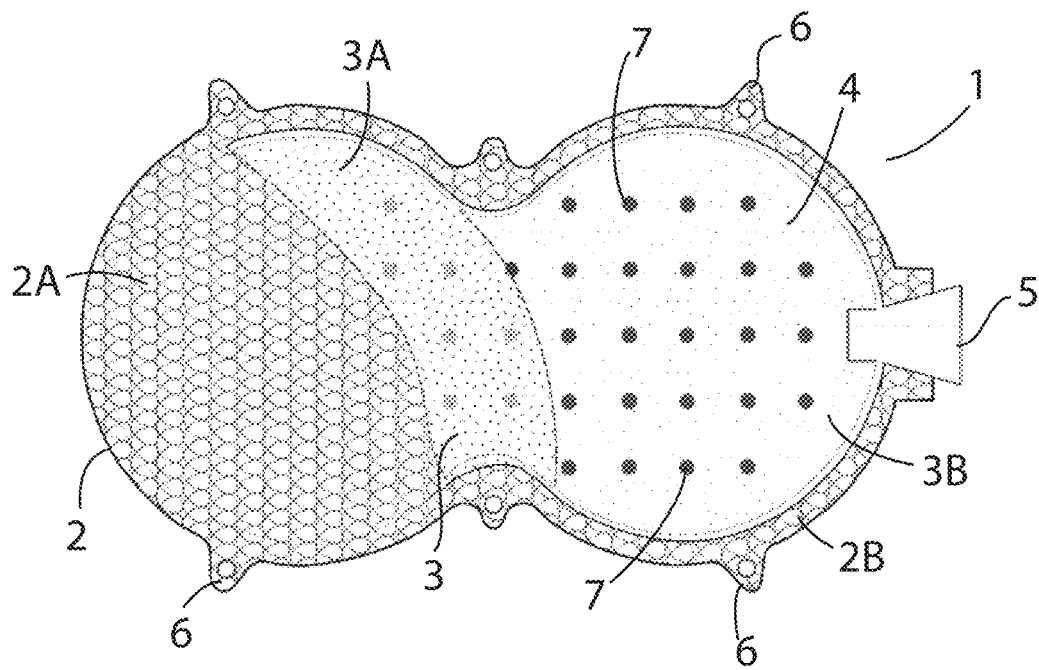
FIG. 7 is a plan, partially cut-away, view of one embodiment of a cell encapsulating device of the invention.

Referring to FIG. 7, a cell encapsulating device of the invention is described and indicated generally with the reference numeral 1. The device 1 has a generally flat structure and comprises an outer macroporous barrier layer 2 comprising two sheets of liquid coil rope scaffold 2A and 2B which form the front and rear faces of the device, and an inner microporous barrier layer 3 formed from two sheets of PDMS 3A and 3B which are sealed together at their periphery to define an inner chamber 4 for encapsulation of cells. The macroporous barrier layer 2 and microporous barrier layer 3 are shown partially cut-away to illustrate the inner chamber 4. An input "duckbill" valve 5 is provided at one end of the device. An inner surface of one of the microporous membranes comprises a plurality of cylindrical spacers 7, intended to maintain spacing in the pouch and prevent void areas forming when the cells are added to the device. Alternative spacers may be provided such as a series of baffles. A plurality of tabs 6 are provided around the periphery of the device which act as surgical attachment points when the device is being implanted in the body.

Figure 8:
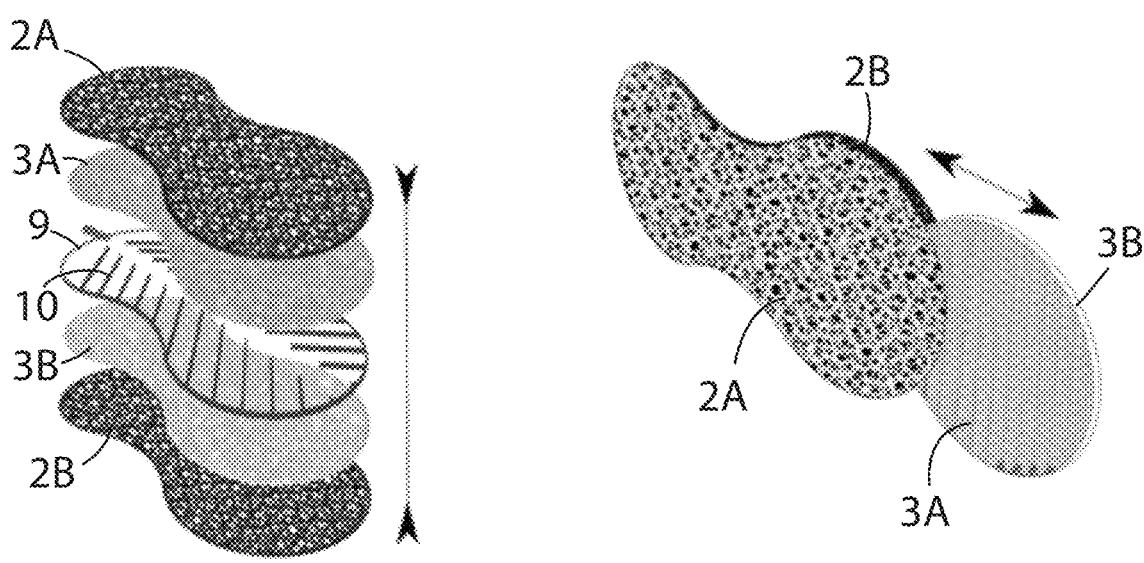
FIG. 8(a) is an exploded of a cell encapsulating device of the invention showing the different layers of the device.
FIG. 8(b) is an exploded view of an alternative embodiment of the device of the invention having an outer macroporous pouch and an inner removable (detachable) microporous cellular pouch.

Referring to FIG. 8, two further embodiments of the cell encapsulation device of the invention are illustrated, in which parts described with reference to the previous embodiment are assigned the same reference numerals.

In the device of FIG. 8A, the rope coil layers 2A and 2B are entirely attached to the inner membranes 3A and 3B, respectively. A cellular framework 8 is provided between the inner membranes 3A and 3B to subdivide the inner chamber into individual cells. The framework 8 comprises an outer perimeter 9 and a series of inwardly-projecting baffles 10 in a "herringbone" shape. The device is fabricated by creating the membranes and inner cellular framework first (i.e. the pouch). Before the salts/poragens are washed out, the rope coil layer is printed on to the surface. The first layer of rope coil will be in direct contact with the membrane and will chemically bond when crosslinked. Further rope coil layers may be added, potentially interspersed with therapeutically active agents such as pro-angiogenic factors.

In the device of FIG. 8B, the rope coil layer and inner pouch are detachable from each other. (This is somewhat akin to a hot-water bottle cover and the hot water bottle.)

This can be achieved by printing the lower layer of rope coil, and crosslinking. A non-permanent or sacrificial insert/separator layer (who's geometry is smaller than the outer perimeter of the rope coil layer) is then inserted. Dissolvable PVA sheet can be used for this purpose. The upper rope coil layer can then be printed on top, and then crosslinked. The separator will prevent the two rope coils layers from bonding together, and result in an open pouch/pocket into which a macroencapsulating (permeable membrane) pouch can be inserted.

The advantage to the second implementation is that the cell containing pouch can be removed, without the need to destroy any vascularisation that has occurred in the implant. This allows for ease of refill should the cells need to be replaced, or if damage occurs to the membrane itself. The sacrificial layer can be fabricated from a water soluble polymer such as PVA or PEG and removed before implantation or alternatively a non degradable polymer which can be inserted with the implant, and remain in place during a period of vascularisation—thus preventing any capillaries from traversing between the two sides and 'stitching' the device closed.

Figure 9:
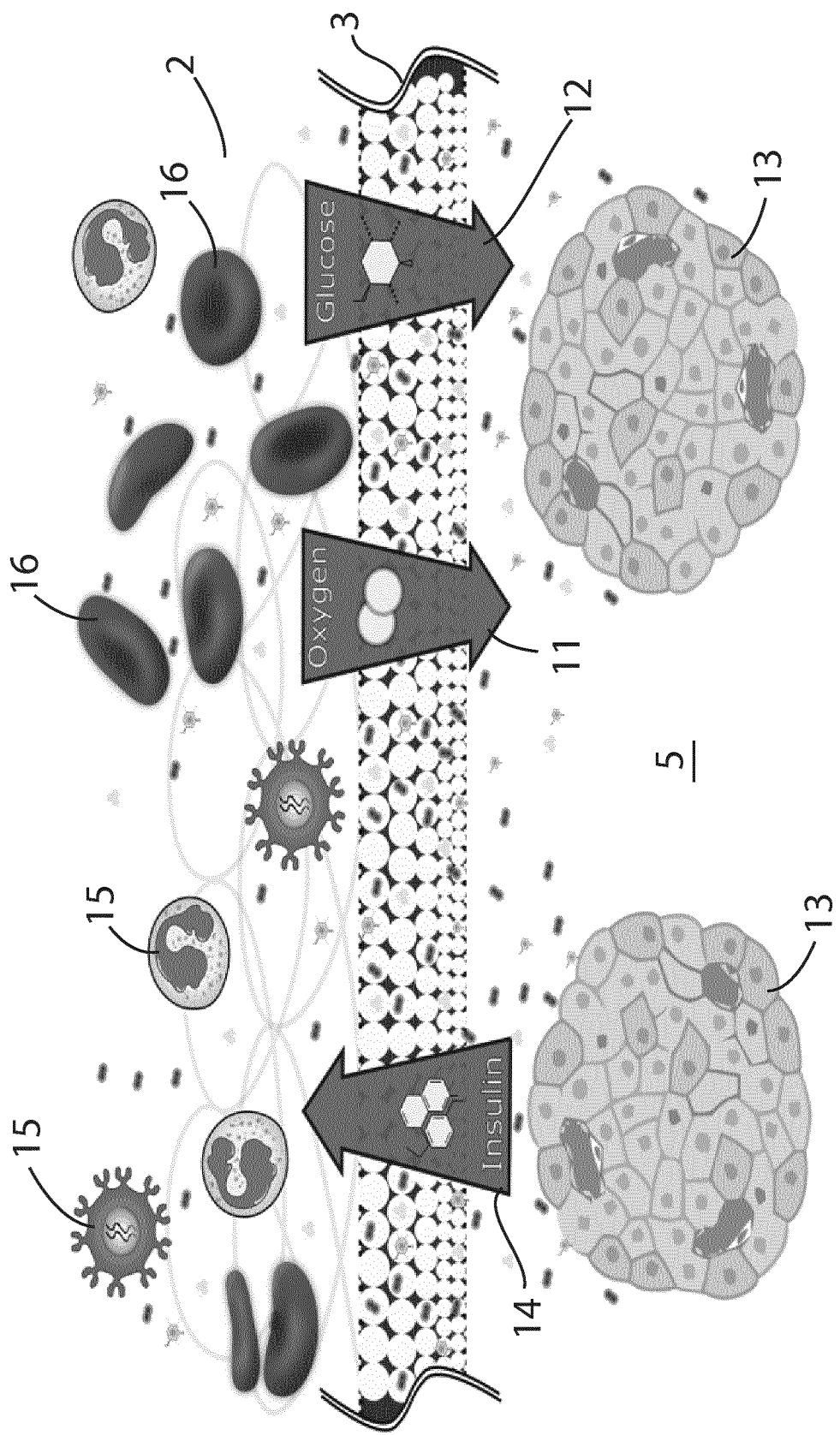
FIG. 9 is an illustration of the barrier layer of the implantable cell encapsulating device of the invention, showing how nutrients and metabolites can pass through the barrier and blood and immune cells are prevented passing through the barrier.

Referring to FIG. 9, an illustration of the use of the device in-vivo is provided in which parts identified with reference to previous embodiments are assigned the same reference numerals. The microporous inner membrane 3 has porosity tailored to allow metabolites such as oxygen 11 and glucose 12 pass into the inner chamber 5 for uptake by Islet cells 13 contained within the chamber 5, and insulin 14 out of the chamber, while preventing cells such as host immune cells 15 pass into the chamber. The outer macroporous rope coil barrier layer 3 has porosity tailored to allow ingress of red blood cells 16 and allow vascularisation to take place within the reticulated matrix. Although not illustrated, the rope coil barrier layer may contain biological growth factors such as VEGF attached to the filaments of the rope coil scaffold.

Figure 10:
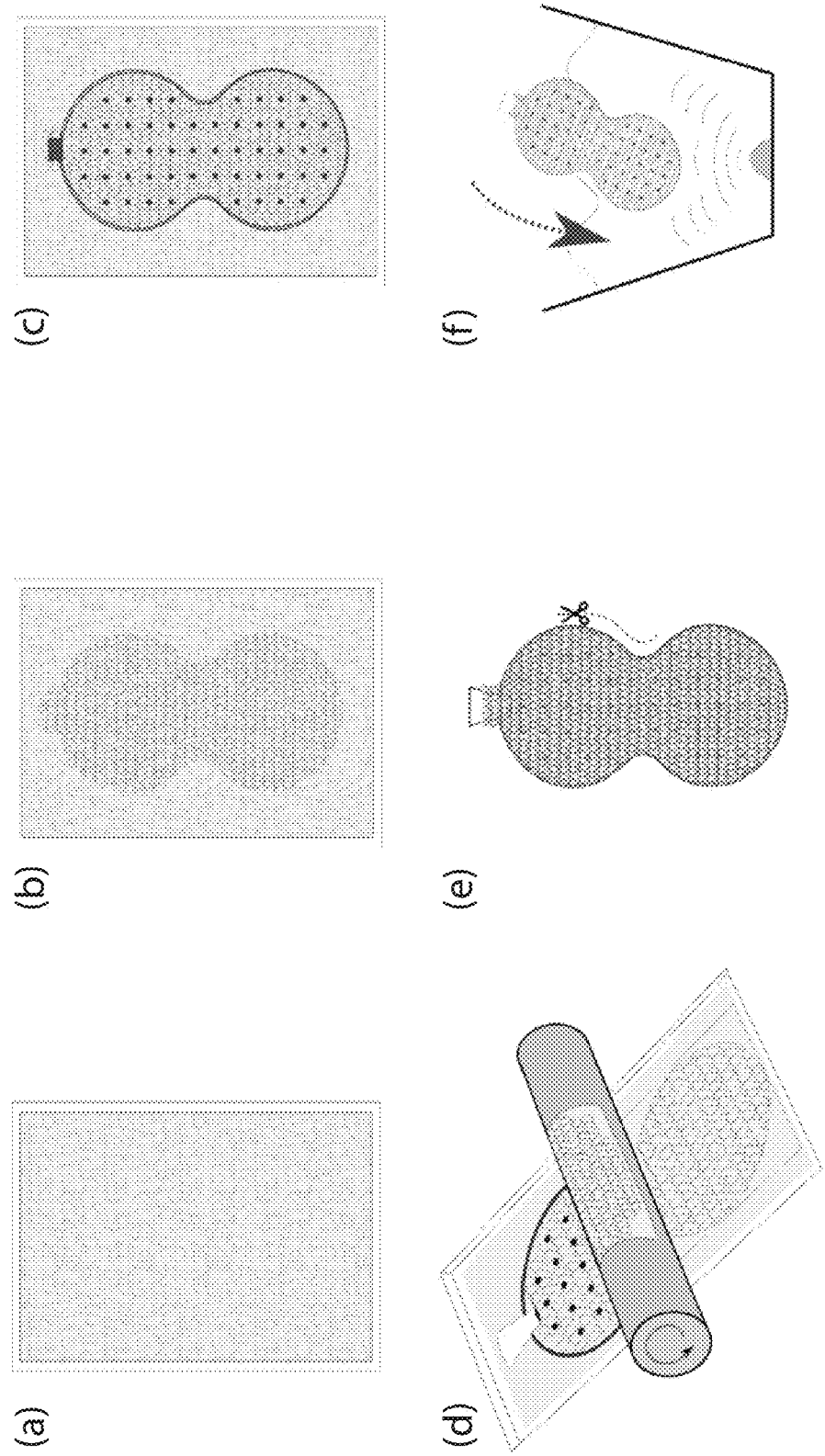
FIG. 10 is an illustration of a process for manufacture of a device of the invention.

Referring the FIG. 10, the fabrication and assembly of an embodiment of an implantable cell encapsulating device of the invention is now described.

1. Two microporous membrane layers are fabricated and crosslinked as detailed in membrane production steps.
2. Two layers of silicone/salt water/PEG mixture is deposited (allowing all solvent and water to evaporate between each layer). (FIG. 9a)
3. A single microporous rope coil layer of NuSil MED4840 silicone is deposited on to the membrane (FIG. 10b)
4. Another two layers of Silicone/Water/PEG mixture is sprayed on top again. This sandwiches the rope coil layer into the membrane.
5. The two uncured silicone membranes are crosslinked at 140° C. (10 minutes).
6. One of the fabricated membranes is then turned over (peeled off the substrate and flipped—what could be referred to as "Smooth side" facing up).
7. The cylindrical inner support structures/spacers and outer perimeter of the device is printed on to the membrane (FIG. 10c)
8. A input port/valve is put in place (FIG. 10d).
9. The second membrane that was fabricated is rolled on to a metal or similar roller, where the "Smooth side" is facing outwards.
10. Place a frame around membrane 1, of a thickness the same height as the support structure and perimeter of step 7. but narrower than the width of the roller.
11. Roll the second membrane over the first, ensuring the perimeter printed silicone is adhering at all points, to create a pouch (FIG. 10d)
12. Heat to 140° C. for 10 minutes to crosslink the inner silicone.
13. Take the pouch and cut off excess membrane using laser cutter or blade. (FIG. 10e)
14. Put into an ultrasonic bath of DI water for 3-6 hours. (FIG. 10f) which washes out the salt and swells the membrane with water (via osmotic pressure) filling the pores in the membranes with water.

As the encapsulated cells will depend on passive oxygen diffusion, an inner thickness of ~400-500 μm would be recommended.

The same silicone or other thixotropic elastomer as was used in the rope coil layers may be used to form the inner support.

A 250-400 um bore dispensing needle is recommended to create the inner support.

Figure 11:
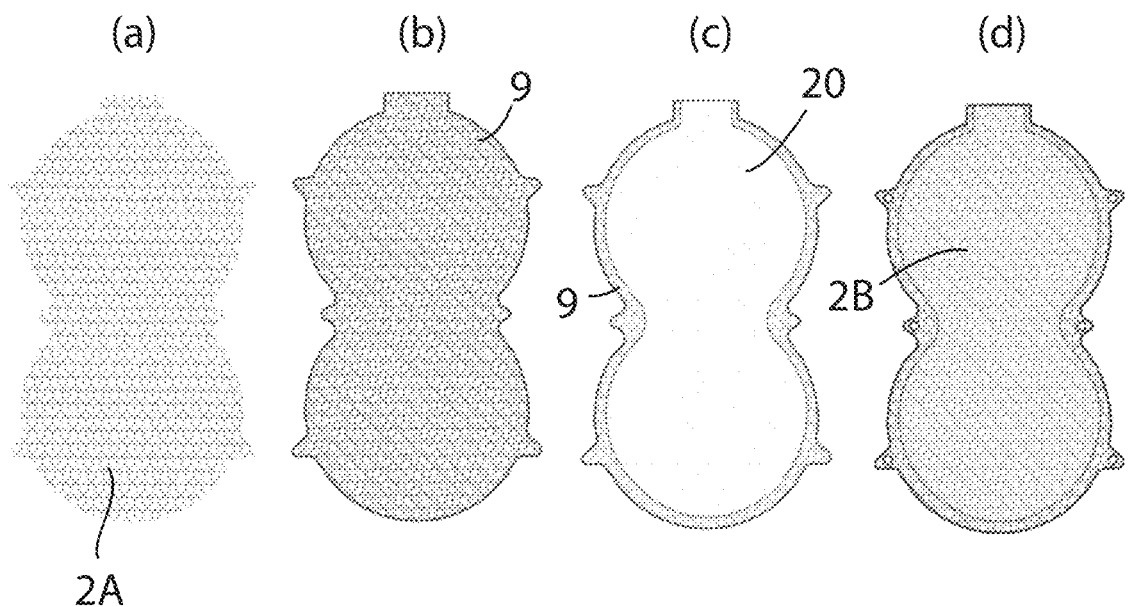
FIG. 11 is an illustration of the layers of the outer pouch of the device of FIG. 8(b) showing the layers of the outer rope coil pouch (a), (b) and (d), and the inner sacrificial layer (c).
Figure 12:
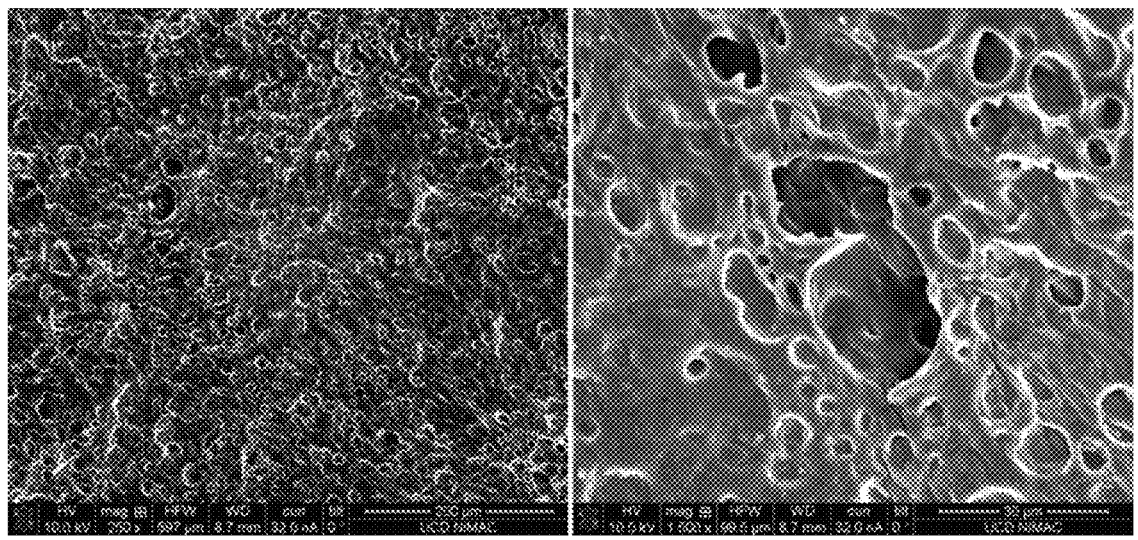
FIG. 12 is an SEM image of a microporous membrane forming part of a device of the invention illustrating the porous structure. The image on the right is a close-up of a larger pore (>10 µm), showing smaller pores embedded inside.
Figure 13:
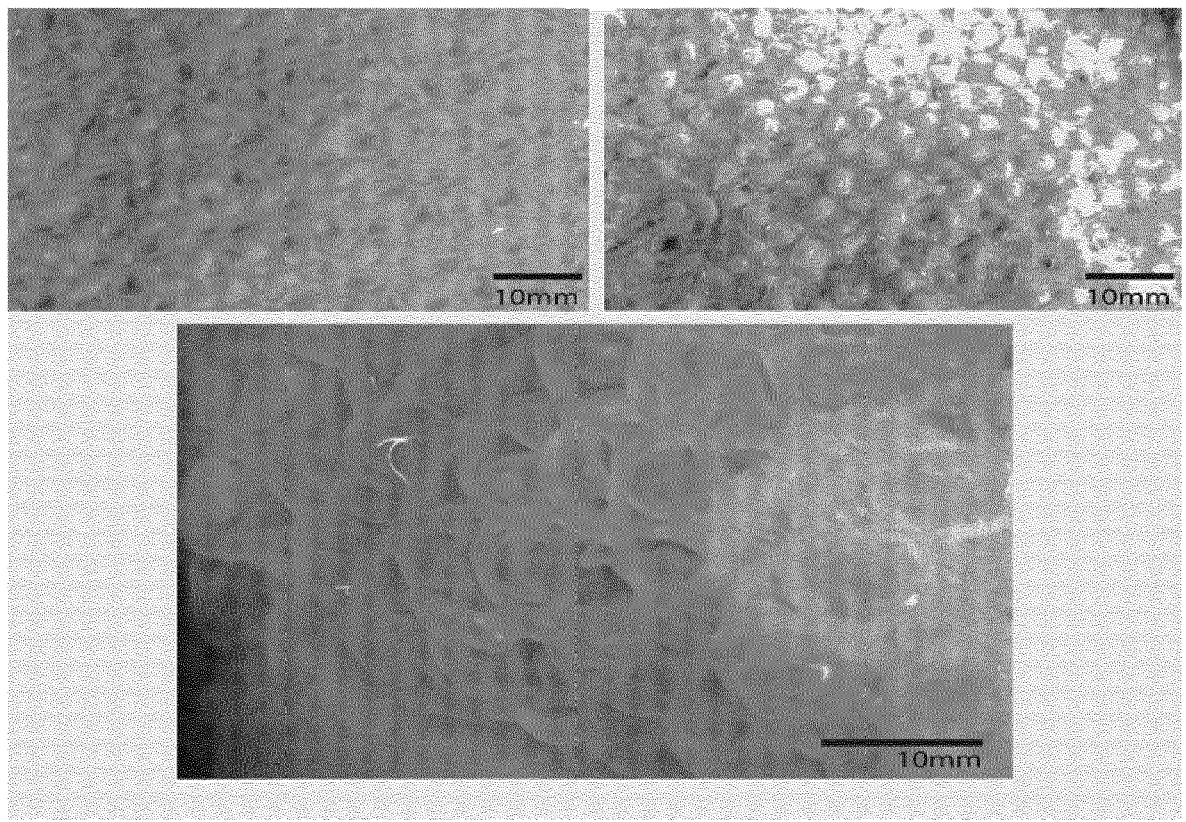
FIG. 13 shows images of the 3-D topology of a membrane.

Referring the FIG. 11, the fabrication and assembly of another embodiment of an implantable cell encapsulating device of the invention is now described.

FIG. 11(a) shows a first liquid rope coil vascularisation layer 2A printed on a surface;

FIG. 11(b) shows the peripheral framework 9 placed around the liquid rope coil layer 2A FIG. 11(c) shows a PVA sacrificial membrane 20 placed on an inside face of the layer 2A inside with the peripheral framework 8

FIG. 11(d) shows a second liquid rope coil vascularisation layer 2B placed on top of the first liquid rope coil 2A and the formation of the outer pouch by sealing the layers to the peripheral framework.

Figure 14:
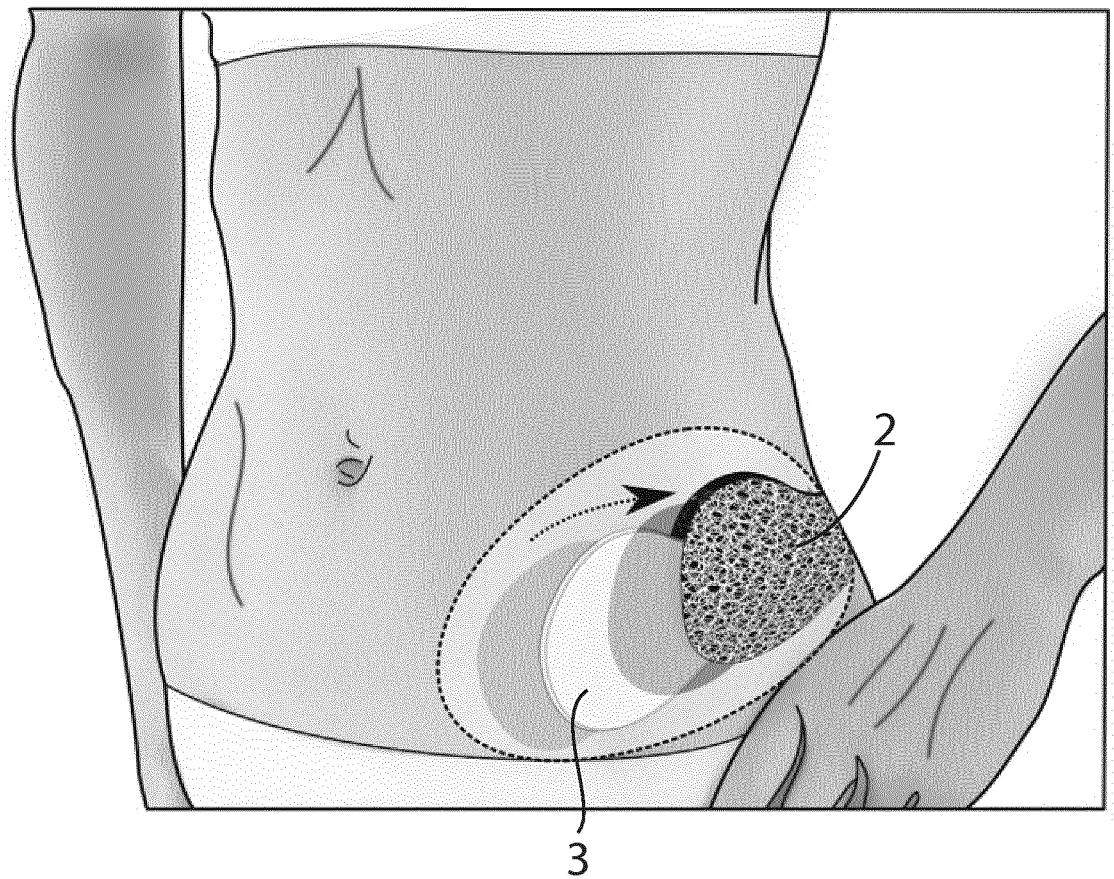
FIG. 14 shows an embodiment of the implantable cell encapsulation device of the invention implanted in the body, where the outer liquid rope coil layer is first implanted and surgically secured in position and allowed to vascularise before the inner microporous pouch containing Islet cells is surgically implanted in the outer pouch.

FIG. 14 shows an embodiment of the implantable cell encapsulation device of FIG. 2B implanted in the body, where the outer liquid rope coil layer is first implanted and surgically secured in position and allowed to vascularise before the inner microporous pouch containing Islet cells is surgically implanted in the outer pouch.

Fabrication of Siloxane Liquid Rope Coil Scaffold

To achieve a stable rope coiled structure, the material must be of sufficiently high viscosity to prevent flow without shear—referred to as slumping.

This can be achieved by mechanically mixing a PDMS with a thixotropic or shear thinning agent to a medical grade elastomer. An example is to add 1-2%/wt Fumed Silica powder, fine Kaolinite powder or a polymeric liquid thixotropic agent such as Dimethyl Siloxane, Dimethyl(propyl (polyethylene oxide))hydroxy)siloxy-terminated.

Alternatively a high viscosity (approx >300,000 cP) medical grade Injection Molding Elastomer such as NuSil MED4840 can be mixed part A&B and used without rheological modification.

The shear thinning elastomer should be loaded into a dispensing cartridge and all air bubbles removed (by centrifugation).

To guarantee constant pore size across the entire surface of the layer the dispensing material cartridge should be loaded on to a constant flow dispensing pump such as a Progressive Cavity Pump or a Positive Displacement Auger Valve based pump. This pump should be mounted on an XYZ CNC gantry such as a 3D printer.

A fine aperture (micro-bore) dispensing nozzle should be attached to the output of the pump. Ideally the nozzle should be a conical tip, rather than needle type to allow faster extrude speeds. The bore and type of nozzle will define both the output filament radius and the maximum fluid dispensing speed achievable before the fluid flow becomes 'choked'. At this point, the material output becomes unpredictable and non-linear.

The pore size (or 'loop frequency') of the layer is defined primarily by: ratio of extruded material (mass flow rate) in relation to the speed of print nozzle over the substrate, both of which measured in mm/sec.

Also crucial is the constant distance of nozzle above the substrate.

On beginning the dispensing of the rope coil layer, the nozzle should be placed as near as possible to the substrate upon which the layer is to be extruded. The pump is switched on to begin extruding, while at the same time the nozzle tip is moved directly away from the substrate in the Z direction (perpendicular to the substrate, at the speed of extrusion). On reaching the desired height (in one example 8 mm, using a 200 μm bore conical needle and mass flow of 300 μl/min) the nozzle is moved at 600 mm/min along the XY plane. This results in continuous touching loops of diameter ~2.1 mm.

The substrate to be covered is in-filled by traversing the print head with lines spaced 2.1 mm apart. When one layer is complete, the angle of in-fill line can be changed (in this case by 60° for each layer) and the process is repeated. With three layers applied the resulting has a final average porosity of ~71%.

After printing multiple criss-cross layers, the silicone/elastomer is crosslinked (via elevated temperature, addition cure or UV crosslinking—depending on material).

The filaments can be made more conducive to vascular ingrowth by reducing the hydrophobicity of the material. This can be achieved by surface modification with plasma, then coating (via for example: spray, or vapor deposition) with a bio-compatible hydrophilic polymer such as PEG.

Alternatively, a biological agent such as fibronectin can be used to coat the rope coil filaments.

Fabrication of Microporous Barrier Layer

1) Create supersaturated solution of $H_2O$ and NaCl (~28% Max). If a higher porosity is required in the final body then a secondary crystal can be dissolved in, eg Sucrose, Glucose or Mannitol, depending on desired pore geometry.
2) Potentially, addition of a Polyethylene glycol (eg PEG 6000 20% solution with $H_2O$) can be added to the Salt solution (at a ratio up to 1:3 with the saturated salt solution). This helps the through pore wettability of the final silicone membrane (i.e. hydrophilic)
3) Add sufficient surfactant with the correct Hydrophylic/Lipophilic Balance (HLB) number according to the oil based solvent used.—eg for a water in heptane emulsion, a HLB of 11.5 is preferred
4) Water suspended fibres, for example nano-crystaline cellulose can be added, if reinforcement of the final membrane is required. This is particularly useful at higher percentage porosity.
5) Mix using mechanical or planetary mixer
6) Separately create a solution of elastomer (eg PDMS) and suitable solvent (Eg. Hexane, Heptane, Xylene etc.), so the viscosity is reduced to a sprayable viscosity. The more solvent used, the thinner each layer of membrane will be deposited. In this case 3:1 solvent to solid is used.
7) Combine the crystal solution porogen and elastomer solvent solution and mix with mechanical or planetary mixer. The length of time that these are mixed for will partly define the final pore size, by increasing the microemulsion level.
8) The final mixture is sprayed on to a heated plate with an atomising spray valve. The temperature should not be so high eg 40-70° C. on the hot-plate so as to boil the solvent, as this will create bubbles of uncontrolled size
9) Sufficient time between each layer should be given (~10-20 mins), so as to remove both solvent and water, and allowing the poragen to nucleate and fully crystallise.
10) To reinforce the membrane, a rope coil layer (of pure NuSil 4840 silicone, without poragen) can be sandwiched between the sprayed membrane layers. For example is two sprayed layers, then a single rope coil layer, followed by another two sprayed layers on top. (Fix 4(b)
11) When a sufficiently thick membrane has been created through repeated layers, the polymer can be crosslinked fully using high temperature.
12) The salts and/or sugars are then dissolved out* of the membrane using DI water and ultrasonic bath. At elevated temperature (FIG. 4(e))

*This step should be carried out when the entire device/pouch has been fabricated including inner support structure.

When the membrane is completely washed free of salt, it will swell in size due to water uptake occouring via osmotic pressure caused by the embedded salt crystals. The combination of non-poragen filled rope coil reinforcement, and swellable membrane will result in a surface morphology scattered with multiple domed areas (see photo FIG. 7). This 3D membrane surface has a vastly increased surface area, with which improves oxygen and nutrient transfer.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A biocompatible implantable medical device comprising a medical device implant and a liquid rope coil scaffold disposed on all or part of a surface of the medical device implant, in which the medical device implant is a stent for a body lumen other than vasculature.

2. A biocompatible implantable medical device according to claim 1, in which the liquid rope coil scaffold is formed from a single polymer filament.

3. A biocompatible implantable medical device according to claim 1 in which the liquid rope coil scaffold is formed from a high viscosity polymer.

4. A biocompatible implantable medical device according to claim 1, in which the liquid rope coil scaffold is formed from a photo-curable polymer.

5. A biocompatible implantable medical device according to claim 1, in which the liquid rope coil scaffold comprises cells incorporated into pores of the scaffold.

6. A biocompatible implantable medical device according to claim 1, formed from a bio-ink comprising a polymer and a therapeutically active agent.

7. An implantable medical device according to claim 1, in which the liquid rope coil scaffold has variable pore size architecture.

8. A biocompatible implantable medical device according to claim 1, in which the stent is a gastrointestinal stent or a stent for the urethra or ureter.

9. A biocompatible implantable medical device according to claim 1, in which the liquid rope coil scaffold has a coil diameter of between 1 and 5 mm.

10. A biocompatible implantable medical device according to claim 1, in which the liquid rope coil is formed from silicone.

* * * * *